(12) United States Patent
Heaton et al.

(10) Patent No.: US 7,312,344 B2
(45) Date of Patent: Dec. 25, 2007

(54) DIMERIC ISOFLAVONES

(75) Inventors: Andrew Heaton, Abbotsford (AU); Graham Edmund Kelly, Northbridge (AU); Naresh Kumar, Maroubra (AU)

(73) Assignee: Novogen Research Pty Limited, New South Wales (AU)

( * ) Notice: Subject to any disclaimer, the term of this patent is extended or adjusted under 35 U.S.C. 154(b) by 81 days.

(21) Appl. No.: 10/469,957

(22) PCT Filed: Mar. 8, 2002

(86) PCT No.: PCT/AU02/00264

§ 371 (c)(1), (2), (4) Date: Mar. 8, 2004

(87) PCT Pub. No.: WO02/070502

PCT Pub. Date: Sep. 12, 2002

(65) Prior Publication Data

US 2004/0152761 A1    Aug. 5, 2004

(30) Foreign Application Priority Data

Mar. 8, 2001    (AU) ............................ PR 3633

(51) Int. Cl.
*C07D 311/00* (2006.01)
(52) U.S. Cl. ........................ 549/406; 514/456
(58) Field of Classification Search ............... 514/432, 514/456; 549/23, 406
See application file for complete search history.

(56) References Cited

U.S. PATENT DOCUMENTS

| | | |
|---|---|---|
| 3,535,344 A | 10/1970 | Irmscher et al. |
| 3,973,608 A | 8/1976 | Umezawa et al. |
| 4,157,984 A | 6/1979 | Zilliken |
| 4,200,692 A | 4/1980 | Puls et al. |
| 4,264,509 A | 4/1981 | Zilliken |
| 4,301,251 A | 11/1981 | Rumyantseva et al. |
| 4,366,082 A | 12/1982 | Zilliken |
| 4,390,559 A | 6/1983 | Zilliken |
| 4,428,876 A | 1/1984 | Iwamura |
| 4,814,346 A | 3/1989 | Albert et al. |
| 5,141,746 A | 8/1992 | Fleury et al. |
| 5,153,230 A | 10/1992 | Jafery |
| 5,247,102 A | 9/1993 | Kállay et al. |

(Continued)

FOREIGN PATENT DOCUMENTS

| | | |
|---|---|---|
| AU | B-80655/87 | 5/1988 |
| AU | A-10227/95 | 7/1995 |
| AU | A-24813/97 | 12/1997 |
| AU | A-73072/98 | 9/1999 |
| AU | A-27714/00 | 11/2000 |
| DE | 44 32 947 A1 | 3/1996 |
| EP | 0129667 A1 | 1/1985 |
| EP | 0135172 A2 | 3/1985 |
| EP | 0136569 A2 | 4/1985 |
| EP | 0426998 A2 | 5/1991 |

(Continued)

OTHER PUBLICATIONS

U.S. Appl. No. 09/546,565, filed Apr. 11, 2000, Kelly et al.
U.S. Appl. No. 09/602,191, filed Jun. 22, 2000, Kelly.

(Continued)

*Primary Examiner*—Amelia A. Owens
(74) *Attorney, Agent, or Firm*—Finnegan, Henderson, Farabow, Garrett, & Dunner, LLP

(57) ABSTRACT

A compound of the general formula (I) or (II) wherein X is O, $NR_4$ or S and $R_1$-$R_8$ are as defined in the specification

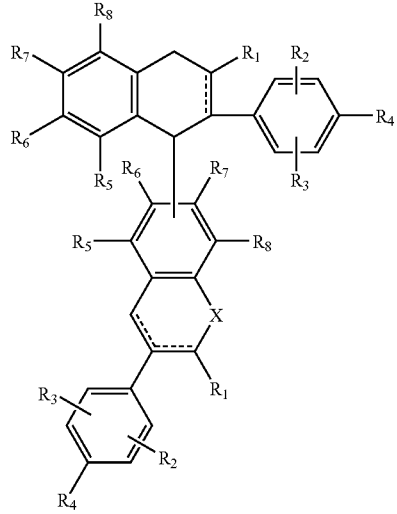

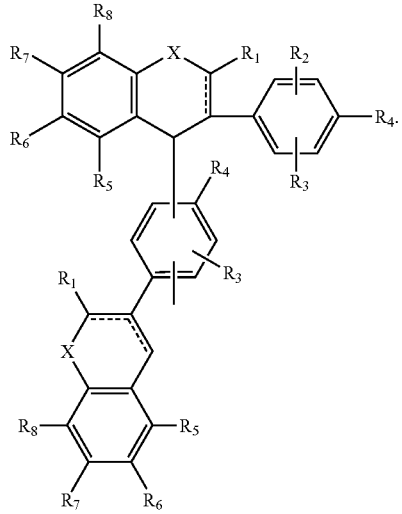

9 Claims, No Drawings

U.S. PATENT DOCUMENTS

| | | |
|---|---|---|
| 5,320,949 A | 6/1994 | Shen |
| 5,352,384 A | 10/1994 | Shen |
| 5,424,331 A | 6/1995 | Shlyankevich |
| 5,498,631 A | 3/1996 | Gorbach et al. |
| 5,506,211 A | 4/1996 | Barnes et al. |
| 5,516,528 A | 5/1996 | Hughes et al. |
| 5,523,087 A | 6/1996 | Shlyankevich |
| 5,530,112 A | 6/1996 | Greenshields et al. |
| 5,547,866 A | 8/1996 | Durzan et al. |
| 5,554,519 A | 9/1996 | Weber et al. |
| 5,569,459 A | 10/1996 | Shlyankevich |
| 5,637,561 A | 6/1997 | Shen et al. |
| 5,639,785 A | 6/1997 | Kung |
| 5,679,806 A | 10/1997 | Zheng et al. |
| 5,700,669 A | 12/1997 | Hanson et al. |
| 5,702,752 A | 12/1997 | Gugger et al. |
| 5,726,034 A | 3/1998 | Bryan et al. |
| 5,733,926 A | 3/1998 | Gorbach |
| 5,763,389 A | 6/1998 | Shen et al. |
| 5,789,581 A | 8/1998 | Matsuura et al. |
| 5,792,503 A | 8/1998 | Gugger et al. |
| 5,804,234 A | 9/1998 | Suh et al. |
| 5,830,887 A | 11/1998 | Kelly |
| 5,855,892 A | 1/1999 | Potter et al. |
| 5,942,539 A | 8/1999 | Hughes, Jr. et al. |
| 6,004,558 A | 12/1999 | Thurn et al. |
| 6,060,070 A | 5/2000 | Gorbach |
| 6,235,773 B1 | 5/2001 | Bissett |
| 6,455,032 B1 | 9/2002 | Kelly et al. |
| 6,497,906 B1 | 12/2002 | Kelly |
| 6,562,380 B1 | 5/2003 | Kelly |
| 6,599,536 B1 | 7/2003 | Kelly et al. |
| 6,642,212 B1 | 11/2003 | Kelly |
| 6,649,648 B1 | 11/2003 | Kelly et al. |
| 2002/0035074 A1 | 3/2002 | Kelly |

FOREIGN PATENT DOCUMENTS

| | | |
|---|---|---|
| EP | 0 671 170 A1 | 9/1995 |
| EP | 0 795 553 A1 | 9/1997 |
| EP | 0 906 761 A2 | 4/1999 |
| FR | 2 693 724 | 1/1994 |
| GB | 1482238 | 8/1977 |
| GB | 1 495 189 A | 12/1977 |
| JP | S50-0035393 | 4/1975 |
| JP | S50-101360 A | 8/1975 |
| JP | S50-160483 A | 12/1975 |
| JP | S61-247396 A | 4/1986 |
| JP | S61-246124 A | 11/1986 |
| JP | S62-106016 A | 5/1987 |
| JP | S62-106017 A | 5/1987 |
| JP | S62-126186 A | 6/1987 |
| JP | H01-042427 A | 2/1989 |
| JP | H01-226824 A | 9/1989 |
| JP | H01-258669 A | 10/1989 |
| JP | H02-067218 A | 3/1990 |
| JP | H02-069165 A | 3/1990 |
| JP | H02-124883 A | 5/1990 |
| JP | H02-160722 A | 6/1990 |
| JP | H03-047049 A | 2/1991 |
| JP | H05-170756 A | 7/1993 |
| JP | H06-040876 A | 2/1994 |
| JP | H06-040909 A | 2/1994 |
| JP | H06-086682 A | 3/1994 |
| JP | H06-321752 A | 11/1994 |
| JP | H07-173148 A | 7/1995 |
| JP | H09-067362 A | 3/1997 |
| JP | H10-059956 A | 3/1998 |
| WO | WO 91/14429 A1 | 10/1991 |
| WO | WO 93/23069 A1 | 11/1993 |
| WO | WO 94/23716 A1 | 10/1994 |
| WO | WO 95/03293 A1 | 2/1995 |
| WO | WO 96/10341 A1 | 4/1996 |
| WO | WO 97/06273 A1 | 2/1997 |
| WO | WO 98/08503 A1 | 3/1998 |
| WO | WO 98/48790 A1 | 11/1998 |
| WO | WO 98/49153 A1 | 11/1998 |
| WO | WO 98/50026 A1 | 11/1998 |
| WO | WO 98/52546 A1 | 11/1998 |
| WO | WO 98/56373 A1 | 12/1998 |
| WO | WO 99/11260 A1 | 3/1999 |
| WO | WO 99/11263 A1 | 3/1999 |
| WO | WO 99/18927 A1 | 4/1999 |
| WO | WO 99/36050 A1 | 7/1999 |
| WO | WO 99/37633 A1 | 7/1999 |
| WO | WO 99/43335 A1 | 9/1999 |
| WO | WO 99/48496 A1 | 9/1999 |
| WO | WO 00/03707 A1 | 1/2000 |
| WO | WO 00/16759 A2 | 3/2000 |
| WO | WO 00/49009 A1 | 8/2000 |
| WO | WO 00/54753 A2 | 9/2000 |
| WO | WO 00/62765 A2 | 10/2000 |
| WO | WO 00/64438 A1 | 11/2000 |
| WO | WO 00/66576 A1 | 11/2000 |
| WO | WO 01/17986 A1 | 3/2001 |
| WO | WO 01/53285 A1 | 7/2001 |
| WO | WO 02/055072 A1 | 7/2002 |
| WO | WO 02/070502 A1 | 9/2002 |
| WO | WO 02/074307 A1 | 9/2002 |

OTHER PUBLICATIONS

U.S. Appl. No. 09/889,701, filed Nov. 5, 2001, Heaton et al.
U.S. Appl. No. 09/986,509, filed Nov. 9, 2001, Kelly.
U.S. Appl. No. 10/176,762, filed Jun. 21, 2002, Kelly et al.
U.S. Appl. No. 10/177,387, filed Jun. 21, 2002, Kelly et al.
U.S. Appl. No. 10/181,549, filed Nov. 7, 2002, Husband et al.
U.S. Appl. No. 10/212,847, filed Aug. 5, 2002, Kelly et al.
U.S. Appl. No. 10/274,371, filed Oct. 21, 2002, Kelly.
U.S. Appl. No. 10/459,537, filed Jun. 12, 2003, Kelly et al.
U.S. Appl. No. 10/471,668, filed Sep. 15, 2003, Husband et al.
U.S. Appl. No. 10/600,004, filed Jun. 18, 2003, Kelly et al.
U.S. Appl. No. 10/611,087, filed Jul. 2, 2003, Kelly.
U.S. Appl. No. 10/611,151, filed Jul. 2, 2003, Kelly.
U.S. Appl. No. 10/636,902, filed Aug. 6, 2003, Kelly et al.
U.S. Appl. No. 10/704,385, filed Nov. 7, 2003, Heaton et al.
U.S. Appl. No. 10/799,022, filed Mar. 11, 2004, Kelly.
Adlercreutz, H. et al., "Determination of Urinary Lignans and Phytoestrogen Metabolites, Potential Antiestrogens and Anticarcinogens, in Urine of Women on Various Habitual Diets," *J. steroid Biochem.*, vol. 25, No. 58, pp. 791-797 (1986).
Adlercreutz, H. et al., "Dietary Phytoestrogens and Cancer: In Vitro and In Vivo Studies," *J. Steroid Biochem. Molec. Biol.*, vol. 41, No. 3-8, pp. 331-337 (1992).
Adlercreutz, H. et al., "Dietary phyto-oestrogens and the menopause in Japan," *The Lancet*, vol. 339, pp. 1233, (May 1992).
Adlercreutz, H. et al., "Effect of Dietary Components, Including Lignans and Phytoestrogens, on Enterohepatic Circulation and Liver Metabolism of Estrogens and on Sex Hormone Binding Globulin (SHBG)," *J. Steroid Biochem*, vol. 27, No. 4-6, pp. 1135-1144 (1987).
Adlercreutz, H. et al., "Excretion of the Lignans Enterolactone and Enterodiol and of Equol in Omnivorous and Vegetarian Postmenopausal Women and in Women with Breast Cancer," *The Lancet*, pp. 1295-1299, (Dec. 1982).
Adlercreutz, H., "Lignans and Phytoesrogens," *Front. gastrointest. Res.*, vol. 14, pp. 165-176, (1988).
Adlercreutz, H. et al., "Urinary excretion of lignans and isoflavonoid phytoestrogens in Japanese men and women consuming a traditional Japanese diet," *Am. J. Clin. Nutr.*, vol. 54, pp. 1093-1100, (1991).
Adlercreutz, H., "Western diet and Western diseases: some hormonal and biochemical mechanisms and associations," *Scand. J. Clin. Lab. Invest*, Suppl. 201, pp. 3-23, (1990).

Akkad, Andrea A., et al., "Abnormal Uterine Bleeding on Hormone Replacement: The Importance of Intrauterine Structural Abnormalities," *Obstetrics & Gynecology*, vol. 86, pp. 330-334 (1995).

Alegrio, L. V. et al.; "Diarylheptanoids and Isoflavonoids from *Centrolobium*Species," *Phytochemistry*, vol. 28, No. 9, pp. 2359-2362, (1989).

Al-Maharik, N.I. et al., "Synthesis of C-C-Bridged Bis-Isoflavones," *J. Org. Chem.*, vol. 65, pp. 2305-2308, (2000).

Alley, M.C. et al., "Feasibility of Drug Screening with Panels of Human Tumor Cell Lines Using a Microculture Tetrazolium Assay," *Cancer Res.* 48, 589-601, (1988).

Anderson M.D., J. et al., "Meta-Analysis of the Effects of Soy Protein Intake on Serum Lipids," *New Eng. J. Med.*, vol. 333, No. 5, pp. 276-282, (Aug. 1995).

Anderson, et al., "Biphasic Effects of Genistein on Bone Tissue in the Ovariectomized, Lactating Rat Model," *P. S. E. B. M.* vol. 217, pp. 345-350, (1998).

Baber, R. et al., "The effect of an isoflavone dietary supplement (Rismostil) on serum lipids, forearm bone density and endometrial thickness in post-menopausal women," *Proc. 10th Annual Meeting of the North American Menopause Society*, New York, Sep. 23-25, 1999.

Bailey, E.T. et al., "Isoflavone Concentrations in the Leaves of the Species of the Genus *Trifolium*, Section *Calycomorphum*," *Aust. J. Agric. Res.*, vol. 22, No. 5, pp. 731-736, (Sep. 1971).

Bannerjee et al., "Polarography of Flavanone and Isoflavone," *J. Electrochem. Soc. India*, vol. 47, No. 4, pp. 237-244, (Oct. 1998).

Bannwart, C. et al., "Identification of the isoflavonic phytoestrogen daidzein in human urine," *Clinica Chimica Acta*, vol. 136, No. 2-3, pp. 165-172, (Jan. 1984).

Barnes, S. et al., "Soybeans Inhibit Mammary Tumors in Models of Breast Cancer," *Mutagens and Carcinogens in the Diet*, pp. 239-253, (1990).

Barrow, N.J., "Nutrient Potential and Capacity: II. Relationship between potassium potential and buffering capacity and the supply of potassium to plants," *Aust. J. Agric. Res.*, vol. 17, No. 6, pp. 849-861, (Nov. 1966).

Barrow, N.J. et al., "Nutrient Potential and Capacity: III: Minimum value of potassium potential for availability to *Trifolium subterraneum*in soil and in solution culture," *Aust. J. Agric. Res.*, vol. 18, pp. 55-62, (1967).

Beck, A.B., "The Oestrogenic Isoflavones of Subterranean Clover," *Aust. J. Agric. Res.*, vol. 15, pp. 223-230, (1964).

Beckham, N., "Estrogenic Activity in Plants—Summary of Talk by Nancy Beckham," from the Brisbane Seminar, 2 pgs., Jan. 1985.

Beckham, N., "Menopause," from *The Family Guide to Natural Therapies*, Greenhouse Publications, Richmond, pp. 41-42 and 50, (1988).

Beckham, N., "Herbal Help to Avoid Menopause Symptoms," *Australian Wellbeing*, No. 29, pp. 74-76, (1988).

Beckham, N., "Phyto-oestrogens and Comounds (sic) that Affect Oestrogen Metabolism—Part I," *Aust. J. Med. Herbalism*, vol. 7, No. 1, pp. 11-16, (1995).

Beckham, N., "Phyto-oestrogens and Compounds that Affect Oestrogen Metabolism—Part II," *Aust. J. Med. Herbalism*, vol. 7; No. 2, pp. 27-33, (1995).

Bennetts, H.W. et al., "A Specific Breeding Problem of Sheep on Subterranean Clover Pastures in Western Australia," *The Australian Veterinary Journal*, vol. 22, pp. 2-12, (Feb. 1946).

Beuker Velasse—Advertising Brochure—with English language translation.

Beylot "Clinical signs of skin ageing," *Revue Francaise de Gynecologie et d'Obstetrique*, (1991) 86/6 (433-441) ISSN: 0035-290X.

Bolger, R. et al., "Rapid Screening of Environmental Chemicals for Estrogen Receptor Binding Capacity," *Environ. Health Perspect.*, 106, 551-7, (1998).

Bombardelli, E., "Chapter 7: Technologies for the Processing of Medicinal Plants," in *The Medicinal Plant Industry*, R.O.B. Wijesekera (Ed.), CRC Press LLC, New York, NY, pp. 85-98, (1991).

Bradbury, R.B. et al., "The Chemistry of Subterranean Clover. Part I. Isolation of Formononetin and Genistein," *J. Chem. Soc.*, pp. 3447-3449, (1951).

Bradbury, R.B. et al., "Estrogens and Related Substances in Plants," in *Vitamins and Hormones: Advances in Research and Applications*vol. XII, R.S. Harris et al. (Eds)., pp. 207-233, (1954).

Braden, A.W.H. et al., "Comparison of Plasma Phyto-Oestrogen Levels in Sheep and Cattle After Feeding on Fresh Clover," *Aust. J. agric. Res.*, vol. 22, pp. 663-670, (1971).

Braden, A.W.H. et al., "The Oestrogenic Activity and Metabolism of Certain Isoflavones in Sheep," *Aust. J. Agric. Res.*, vol. 18, pp. 335-348, (1967).

Bradley, P.R. (Ed.), "Contents" and "Index," in *British Herbal Compendium*, vol. 1: A handbook of scientific information on widely used plant drugs, British Herbal Medicine Association, Bournemouth, Dorset, pp. 5, 231-239, (1992).

Brandi, M.L., "Flavonoids: biochemical effects and therapeutic applications," *Bone and Mineral*, vol. 19 (Suppl.), pp. S3-S14, (1992).

Burali, C. et al., "Synthesis and Anti-Rhinovirus Activity of Halogen-Substituted Isoflavenes and Isoflavans," *European Journal of Medicinal Chemistry*, Editions Scientifique Elsevier, Paris, FR, 22(2):119-123 (Apr. 1987).

Buzzell, R.I. et al., "Inheritance of Flavonol Glycosides in Soybeans," *Can. J. Genet. Cytol.*, vol. 15, pp. 865-867, (1973).

Cassady, J.M. et al., "Use of a Mammalian Cell Culture Benzo($a$)pyrene Metabolism Assay for the Detection of Potential Anticarcinogens from Natural Products: Inhibition of Metabolism by Biochanin A, an Isoflavone from *Trifolium pratense*L.," *Cancer Research*, vol. 48 (22) pp. 6257-6261, (Nov. 1998).

Caswell, A. (ed), "Hypolipidaemic Agent," MIMS Annual, 23rd edition, pp. 2-152 to 2-169, Singapore (1999).

Chan, K. et al., "Inhibitors of hydroxymethylglutaryl-coenzyme A reductase and risk of fracture among older women," *Lancet*; 355(9222):2185-8, Jun. 24, 2000.

Chang et al., "Metabolites of daidzein and genistein and their biological activities," *Journal of Natural Products*, 58(12), pp. 1901-1905, ISSN: 0163-3864, (1995).

Chang Y., "Microwave-Mediated Synthesis of Anticarcinogenic Isoflavones from Soybeans," *J Argric Food Chem*.1994, 42: 1869-1871.

Chicago Center for Clinical Research, Company Press Release Mar. 13, 2000, "Chicago Center for Clinical Research Study suggests New, More Effective Way to Treat Older Women with High Cholesterol."

Circle, S. J. et al., "Processing Soy Flours, Protein Concentrates, and Protein Isolates," in *Soybeans: Chemistry and Technology, vol. 1: Proteins*, A.K. Smith et al. (Eds.), Avi Publishing Company, Inc., Westport, CT, pp. 294-338, (1972).

Clifton-Bligh, P. et al., "The effect of isoflavones extracted from red clover (Rimostil) on lipid and bone metabolism," *Menopause*(in submission), pp. 1-27, 2000.

Collins, B.M. et al., "The estrogenic and antiestrogenic activities of phytochemicals with the human estrogen receptor expressed in yeast," *Steroids*, vol. 62, pp. 365-372, (Apr. 1997).

Coward, L. et al., "Genistein, Daidzein, and Their ꓱ-Glycoside Conjugates: Antitumor Isoflavones in Soybean Foods from American and Asian Diets," *J. Agric. Food Chem.*, vol. 41, No. 11, pp. 1961-1967, (Nov. 1993).

Culbreth, David M.R. (Ed.), *A Manual of Materia Medica and Pharmacology*, Eclectic Medical Publications, Portland, OR, pp. 19-22, (1922).

Davies, H.L. et al., "Further Studies on Oestrogenic Activity in Strains of Subterranean Clover (*Trifolium Subterraneum*L.) In South-Western Australia," *Aust. J. Agric. Res.* vol. 16, No. 6, pp. 937-950, (Nov. 1965).

Davis, H. et al., "Extraction," from *Bentley's Text-Book of Pharmaceuticals*, 6th ed., Chapter XVIII, pp. 272-273, (1956).

Deschamps-Vallet, C. et al., "Transformation Du Cation Isoflavylium en Phenyl-3 Coumarines, Isoflavenes-3 et Isoflavannes," *Tetrahedron Letters*, 24(37):3993-3996 (1983).

Dewick, P.M. "5: Isoflavonoids,", *The Flavonoids: Advances in Research Since 1986*, Ed. by J. B. Harborne, Published by Chapman & Hall, London, pp. 117-138.

Doren, M. et al., "Identification and Treatment of Postmenopausal Women at Risk for the Development of Osteoporosis," *International Journal of Clinical Pharmacology, Therapy and Toxicology*, vol. 20, No. 11, pp. 431-433 (1992).

Dubey et al., "Phytoestrogens Inhibit Growth and MAP Kinase Activity in Human Aortic Smooth Muscle Cells," *Hypertension*, vol. 33 (part II), pp. 177-182, (1999).

Düker, E. et al., "Effects of Extracts from *Cimicifuga racemosa* on Gonadotropin Release in Menopausal Women and Ovariectomized Rats," *Planta Med.*, vol. 57, pp. 420-424, (1991).

Eldridge, A.C., "Determination of Isoflavones in Soybean Flours, Protein Concentrates, and Isolates," *J. Agric. Food. Chem.*, vol. 30, No. 2, pp. 353-355, (1982).

Eldridge, A.C., "High-performance liquid chromatography separation of soybean isoflavones and their glucosides," *J. Chromatography*, vol. 234 pp. 494-496, (1982).

Eldridge, A.C. et al., "Soybean Isoflavones: Effect of Environment and Variety on Composition," *J. Agric. Food Chem.*, vol. 31 pp. 394-396, (1983).

Ellis, G.P. (ed.); "Chromenes, Chromanones, and Chromones"; pp. 256-260; published by John Wiley & Sons, 1977.

EPO Communication dated Mar. 8, 2002 issued for Application No. EP 93 909 679.8.

EPO Supplemental Partial Search Report issued for Application No. EP 99 91 2976.

Evans, D. et al., "Ovarian Cancer Family and Prophylactic Choices," *Journal of Medical Genetics*, pp. 416-418, 1991.

Evans, M. et al., "Hormome Replacement Therapy: Management of Common Problems," *Mayo Clin. Proc*, vol. 70, pp. 800-805, (1995).

Fanti et al., "The Phytoestrogen Genistein Reduces Bone Loss in Short-Term Ovariectomized Rats," *Osteoporosis Int.*, vol. 8, pp. 274-281, (1998).

Farmakalidis, E. et al., "Isolation of 6"-O-Acetylgenistin and 6"-O-Acetyldaidzin from Toasted Defatted Soyflakes," *J. Agric. Food Chem*, vol. 33, pp. 385-389 (1985).

Farmakalidis, E. et al., "Semi-preparative high-performance liquid chromatographic isolation of soybean isoflavones," *J. Chromatography*, vol. 295, pp. 510-514, (Jul. 1984).

Farnsworth, N.R. et al., "Potential Value of Plants as Sources of New Antifertility Agents II," *J. Pharm. Sciences*, vol. 64, No. 5, pp. 717-753, (May 1975).

Francis., C.M. et al., "The Distribution of Oestrogenic Isoflavones in the Genus *Trifolium*," *Aust. J. Agric. Res.*, 18(1):47-54, (Jan. 1967).

Francis, C.M. et al., "Varietal Variation in the Isoflavone Content of Subterranean Clover: Its Estimation by a Microtechnique," *Aust. J. Agric. Res.*, vol. 16, No. 4, pp. 557-564, (Jul. 1965).

Gaynor, J.D. et al., "HPLC Separation and Relative Quantitation of Kaempferol Glycosides in Soybean," *Chromatographia*, vol. 285, No. 12, pp. 1049-1053, (Dec. 1988).

Gildersleeve, R.R. et al., "Screening Rose Clover and Subterranean Clover Germplasm for Isoflavones," *Crop Sci.*, vol. 31, No. 5, pp. 1374-1376, (Sep.-Oct. 1991).

Gildersleeve, R.R. et al., "Detection of Isoflavones in Seeding Subterranean Clover," *Crop Sci.*, vol. 31, pp. 889-892, (Jul.-Aug. 1991).

Gladstones, J.S., "Naturalized Subterranean Clover Strains in Western Australia: A Preliminary Agronomic Examination," *Aust. J. agric. Res.*, vol. 18, No. 5, pp. 713-731, (Sep. 1967).

Goh, J.T.W. et al., "Postmenopausal Endometrioma and Hormonal Replacement Therapy," *Aust NZ J. Obstet Gynaecol*, vol. 32, pp. 384-385 (1992).

Graham, T. L., "Flavonoid and Isoflavonoid Distribution in Developing Soybean Seedling Tissues and in Seed and Root Exudates," *Pharm. Physiol.*, vol. 95, pp. 594-603, (1991).

Grunert E. et al., "Isoflavone in einigen Weiβ- und Rotkleesorten und ihre oestrogene Wirksamkeit bei juvenilen Mäusen," *Deutsche Tierärztliche Wochenschrift*, 74. Jahrgang 1967, p. 431-433.

Herbert, P. et al., (1997), "Cholesterol lowering with statin drugs, risk of stroke, and total mortality. An overview of randomized trials," *JAMA* 278(4):313-21.

Herman, C. et al., "Soybean Phytoestrogen Intake and Cancer Risk," *American Institute of Nutrition*, pp. 757S-770S, (1995).

Hodgson, J. et al., "Supplementation with isoflavonoid phytoestrogens does not alter serum lipid concentrations: a randomised controlled trial in humans," Journal of Nutrition, 128: 728-332, (1998).

Holt, S., "Selected Bibliography of Scientific Studies on Genistein and Other Soya Isoflavones," Soya for Health: The Definitive Medical Guide, Mary Ann Liebert, Inc., Larchmont, NY, pp. 159-170, (1996).

Hulley, S. et al., (1998), "Randomized trial of estrogen plus progestin for secondary prevention of coronary heart disease in postmenopausal women," *JAMA* 280(7): 605-613.

Inoue, N., 1964, "Studies of Synthetic Isoflavones. V. The Reduction of Isoflavone," originally from *Bull. Chem. Soc. Japan*, May 1964, 37(5):601-605, cited in STN International, CAPLUS database, (Columbus, Ohio), No. 61: 32297 (2 pages).

Jenkins, D.J.A. et al., "Leguminous seeds in the dietary management of hyperlipidemia," *Am. J. Clin. Nut.*, vol. 38, pp. 567-573, (1983).

Joannou, G.E. et al., "A Urinary Profile Study of Dietary Phytoestrogens. The Identification and Mode of Metabolism of New Isoflavonoids," *J. Steroid Biochem. Molec. Biol.*, vol. 54, No. 3/4, pp. 167-184, (1995).

Jones, A.E. et al., "Development and Application of a High-performance Liquid Chromatographic Method for the Analysis of Phytoestrogens," *J. Sci. Food Agric.*, vol. 46, pp. 357-364, (1989).

Jurd, L. et al.; "Phenolic and Quinoidal Constituents of Dalbergia Retusa," *Tetrahedron Letters*, vol. 21, pp. 2149-2152; (1972).

Kaldas, R.S. et al., "Reproductive and General Metabolic Effects of Phytoestrogens in Mammals," *Reproductive Toxicology*, vol. 3, No. 2, pp. 81-89, (1989).

Kao, Y., et al., "Molecular Basis of the Inhibition of Human Aromatase (Estrogen Synthetase) by Flavone and Isoflavone Phytoestrogens: A Site-directed Mutagenesis Study," *Environmental Health Perspectives*, vol. 106, No. 2, pp. 85-92 (1998).

Kelly et al., "Metabolites of dietary (soya) isoflavones in human urine," *Clinica Chimica Acta* 223(1-2), pp. 9-22 (Dec. 31, 1993).

Kelly, S. A. et al., "Protein Tyrosine Phosphorylation Mediates TNF-Induced Endothelial-Neutrophil Adhesion in Vitro," *The American Physiological Society*, 274 (2Pt2), pp. H513-H519, (1998).

Kelly, G. et al., "Standarized Red Clover Extract Clinical Monograph," Natural Products Research Consultants, Inc., Seatle, WA, pp. 3-12, (1998).

Kitada, Y. et al., "Determination of isoflavones in soy bean by high-performance liquid chromatography with amperometric detection," *J. Chromatography*, vol. 366, pp. 403-406, (1986).

Kitts, D.D. et al., "Uterine Weight Changes and $^3$H-Uridine Uptake in Rats Treated wtih Phytoestrogens," *Can. J. Anim. Sci.*, vol. 60, pp. 531-534, (Jun. 1980).

Knuckles, B.E. et al., "Coumestrol Content of Fractions Obtained during Wet Processing of Alfalfa," *J. Agric. Food Chem.*, vol. 24, No. 6, pp. 1177-1180, (Nov.-Dec. 1976).

Kudou, S et al., "A New Isoflavone Glycoside in Soybean Seeds (*Glycine max* MERRILL), Glycitein 7-O-β-D-(6"-O-Acetyl)-Glucopyranoside," *Agric. Biol. Chem.*, vol. 55, No. 3, pp. 859-860, (1991).

Kudou, S. et al., "Malonyl Isoflavone Glycosides in Soybean Seeds (*Glycine max* MERRILL)," *Agric. Biol. Chem.*, vol. 55, No. 9, pp. 2227-2233, (1991).

Lamberton, et al., "Catalytic Hydrogenation of Isoflavones. the Preparation of (±)-Equol and Related Isoflavans," *Aust. J. Chem.*, vol. 31, pp. 455-457, (Feb. 1978).

Liepa, A.J., "A Synthesis of Hydroxylated Isoflavylium Salts and Their Reduction Products," *Aust. J. Chem.*, vol. 34, pp. 2647-2655, (1981).

Lindner, H.R., "Study of the Fate of Phyto-Oestrogens in the Sheep by Determination of Isoflavones and Coumestrol in the Plasma and Adipose Tissue," *Aust. J. Agric. Res.*, vol. 18, pp. 305-333, (1967).

Lindner, H.R., "V/1 Occurrence of Anabolic Agents in Plants and their Importance," Environmental Quality and Safety Supplement, Thieme, Stuttgart, Germany, 1976, 5: 151-158.

Liu, Y. et al., "Abstract No. 78763p; Effects of solid dispersion of diadzein on the blood pressure of spontaneously hypersensitive rats," Chemical Abstracts, vol. 155, No. 8, p. 466 (Aug. 26, 1991).

Lock, M., "Contested meanings of the menopause," The Lancet, vol. 337, pp. 1270-1272, (May 25, 1991).

Mäkelä, S., et al., "Inhibition of 17β-Hydroxysteroid Oxidoreductase by Flavonoids in Breast and Prostate Cancer Cells," pp. 310-316 (1998).

May, M. J. et al., "Effects of Protein Tyrosine Kinase Inhibitors on Cytokine-Induced Adhesion Molecule Expression by Human Umbilical Vein Endothelial Cells," British Journal of Pharmacology, No. 118, pp. 1761-1771, (1996).

Mazur et al.; "Natural and anthropogenic environmental oestrogens: the scientific basis for risk assessment* -Naturally occurring oestrogens in food," Pure & Appl. Chem.70(9), pp. 1759-1776 (1998).

Mazur et al., "Isolfavonoids and lignans in legumes: Nutritional and health aspects in humans," Nutritional Biochemistry9, pp. 193-200 (1998).

The Merck Index, 8th Ed., "Daidzein," "Formononetin," and "Geinstein," pp. 320, 484, and 469-470 [respectively], Merck & Co., Inc., (1968).

Messina, M. et al., "The Role of Soy Products in Reducing Risk of Cancer," J. of National Cancer Institute, vol. 83, No. 8, pp. 541-546, (Apr. 17, 1991).

Morris, P. et al., "Identification and accumulation of isoflavonoids and isoflavone glucosides in soybean leaves and hypocotyls in resistance responses to Phytophthora megaspermaf.sp. glycinea," Physiological and Molecular Plant Pathology, vol. 39, pp. 229-244, (1991).

Mowrey, D.B., "Introduction," in Next Generation Herbal Medicine: Guaranteed Potency Herbs, 2ndEdition, Keats Publishing, Inc., New Canaan, CT, pp. 3-13, (Jan. 1990).

Murphy, P.A., "Phytoestrogen Content of Processed Soybean Products," Food Tecchnology, pp. 60-64, (Jan. 1982).

Murphy, P.A., "Separation of genistin, daidzin and their aglucones, and cournesterol by gradient high-performance liquid chromatography," J. Chromatography, vol. 211, No. 1, pp. 166-169, (1981).

Naim, M. et al., "A New Isoflavone from Soya Beans," Phytochemistry, vol. 12, pp. 169-170, (1973).

Naim, M., "The Isolation, Characterization and Biological Activity of Isoflavones from Soybeans," Submitted to the Senate of the Hebrew University of Jerusalem—Oct. 1974.

Naim, M. et al., "Soybean Isoflavones. Characterization, Determination, and Antifungal Activity," J. Agr. Food Chem., vol. 22, No. 5, pp. 806-810, (1974).

Namnoum, A.B., et al., "Incidence of symptom recurrence after hysterectomy for endometriosis," Fertility and Sterility, vol. 64, No. 5, pp. 898-902 (1995).

Nash, A.M. et al., "Fractionation and Characterization of Alcohol Extractables Associated with Soybean Proteins. Nonprotein Components," J. Agr. Food Chem., vol. 15, No. 1, pp. 102-108, (Jan.-Feb. 1967).

Nestel, P. et al., (1997), "Soy isoflavones improve systemic arterial compliance but not plasma lipids in menopausal and peri-menopausal women," Arteriosclerosis, Thrombosis and Vascular Biology17:3392-3398.

Nestel, P. et al., (1999), "Isoflavones from red clover improves systemic arterial compliance but not plasma lipids in menopausal women," Journal of Clinical Endocrinology and Metabolism84: 895-898.

Ohta, N. et al., "Isoflavonoid Constituents of Soybeans and Isolation of a New Acetyl Daidzin," Agric. Biol. Chem., vol. 43, No. 7, pp. 1415-1419, (1979).

Okano, K. et al., "Isolation of Four Kinds of Isoflavon from Soya Bean (abstract)," Bull. Agr. Chem. Soc. Japan, vol. 15, Nos. 172-183p. 110, (1939).

Okubo, K. et al., "Components Responsible for the Undesirable Taste of Soybean Seeds," Biosci. Biotech. Biochem., vol. 56, No. 1, pp. 99-103, (1992).

Palmetshofer, A. et al., "α-Galactosyl Epitope-Mediated Activation of Porcine Aortic Endothelial Cells", Transplantation, vol. 65, No. 7, pp. 971-978, (Apr. 15, 1998).

Panchagnula, R. et al., "Transdermal iontophoresis revisited," Curr. Opin. Chem. Biol, 2000 Aug. 4(4):468-73.

Parfitt, K., Martindale 32nd edition, "The complete drug reference," (1999), 32nd Edition,. Pharmaceutical Press, London, pp. v. and vi.

PCT Search Report issued for Application No. PCT/AU00/01056 dated Nov. 27, 2000.

Peterson, G. et al., "Genistein and Biochanin A Inhibit the Growth of Human Prostate Cancer Cells but not Epidermal Growth Factor Receptor Tyrosine Autophosphorylation," The Prostate, vol. 22, No. 4, pp. 335-345, (1993).

Peterson, G. et al., "Genistein Inhibition of the Growth of Human Breast Cancer Cells: Independence From Estrogen Receptors and the Multi-drug Resistance Gene," Biochemical and Biophysical Research Communications, vol. 179, No. 1, pp. 661-667, (Aug. 1991).

Pope, G.S., "The Importance of Pasture Plant Oestrogens in the Reproduction and Lactation of Grazing Animals," Dairy Science Abstracts, vol. 16, No. 5, pp. 333-356, (May 1954).

Potter, S. et al., "Soy protein isoflavones: their effect on blood lipids and bone density in postmenopausal women," American Journal of Clinical Nutrition, 68(Suppl):1375S-1379S (1998).

Price, K.R. et al., "Naturally occurring oestrogens in foods—A review," Food Additives and Contaminants, vol. 2, No. 2, pp. 73-106, (1985).

Reinli, K. et al., "Phytoestrogen Content of Foods—A Compendium of Literature Values," Nutrition and Cancer, vol. 26, No. 2, pp. 123-148, (1996).

Rose, D.P., "Dietary Fiber, Phytoestrogens, and Breast Cancer," Nutrition, vol. 8, No, 1, pp. 47-51, (Jan.-Feb. 1992).

Rossiter, R.C. et al., "Physiological and Ecological Studies on the Oestrogenic Isoflavones in Subterranean Clover (T. subterraneumL.), III: Effects of Light," Aust. J. Agric. Res., vol. 18, No. 1, 23-37, (Jan. 1967).

Rossiter, R.C., "Physiological and Ecological Studies on the Oestrogenic Isoflavones in Subterranean Clover (T. subterraneumL.), IV: Effects of Zinc Deficiency in Clover Seedlings," Aust. J. Agric. Res., vol. 18, No. 1, 39-46, (Jan. 1967).

Sacks, F. et al., (1996), "The effect of pravastatin on coronary events after myocardial infarction in patients with average cholesterol levels," Cholesterol and Recurrent Events Trial Investigators, New England Journal of Medicine, 335(14):1001-9.

Samman, S. et al., (1999), "The effect of supplementation with isoflavones on plasma lipids and oxidisability of low density lipoprotein in pre-menopausal women," Atherosclerosis147:277-283.

Sanchez-Guerrero, J. et al., "Postmenopausal Estrogen Therapy and the Risk for Developing Systemic Lupus Erythematosus," Annals of Internal Medicine,vol. 122, No. 6, pp. 430-433 (1995).

Sbarouni, E. et al., (1998), "The effect of hormone replacement therapy alone and in combination with simvastatin on plasma lipids of hypercholesterolemic postmenopausal women with coronary artery disease," Journal of the American College of Cardiology32(5): 122-50.

Scandinavian Simvastation Survival Study Group, (1994), "Randomised trial of cholesterol lowering in 4444 patients with coronary heart disease: the Scandinavian Simvastatin Survival Study (4S)," Lancet344:1383-89.

Schultz, "Isoflavonglucoside Formononetin-7-glucosid und Biochanin A-7-glucosid in Trifolium pratense L.," Die Naturwissenschaften, 52(18), p. 517, Sep. 1965.

Scudiero, D.A. et al., "Evaluaion of a Soluble Tetrazolium/formazan Assay for Cell Growth and Drug Sensitivity in Culture Using Human and Other Tumor Cell Lines," Cancer Research48, 4827-4833 (1988).

Sener, A.B., et al., "The effects of hormone replacement therapy on uterine fibroids in postmenopausal women," Fertility and Sterility, vol. 65, No. 2, pp. 354-357 (1996).

Seo, A. et al., "Improved High-Performance Liquid Chromatographic Analysis of Phenolic Acids and Isoflavonoids from Soybean Protein Products," *J. Agric. Food Chem.*, vol. 32, No. 3, pp. 530-533, (1984).

Setchell, K.D.R. et al., "High-Performance Liquid Chromatographic Analysis of Phytoestrogens in Soy Protein Preparations with Ultraviolet, Electrochemical and Thermospray Mass Spectrometric Detection," *J. Chromatography*, vol. 386 pp. 315-345, (1987).

Setchell, K.D.R. et al., "14: Mammalian Lignans and Phytooestrogens Recent Studies on their Formation, Metabolism and Biological Role in Health and Disease," in *Role of the Gut Flora in Toxicity and Cancer*, I.R. Rowland (Ed.), Academic Press, Inc., San Diego, CA, pp. 315-339, (1988).

Setchell, K.D.R. et al., "Nonsteroidal estrogens of dietary origin: possible roles in hormone-dependent disease," *Am. J. Clin. Nut.*, vol. 40, pp. 569-578, (1984).

Sharma, R.D., "Effect of Various Isoflavones on Lipid Levels in Triton-treated Rats," *Atherosclerosis*33, 1979, p. 371-375.

Shen, F. et al. "Tamoxifen and Genistein Synergistically Down-regulate Signal Transduction and Proliferation in estrogen Re eptor-negative human breast Carcinoma MDA-MB-435 Cells," *Anticancer Research*19, 1657-1662 (1999).

Shimoyamada, M. et al., "Saponin Composition in Developing Soybean Seed (*Glycine max*(L.) MERRILL, cv. Mikuriyaao)," *Agric. Biol. Chem.*, vol. 55, No. 5, pp. 1403-1405, (May 1991).

Shutt, Donald A., "The effects of plant oestrogens on animal reproduction," *Endeavour*, vol. 35, pp. 110-113, (1976).

Shutt, D.A. et al., "Free and Conjugated Isoflavones in the Plasma of Sheep Followed Ingestion of Oestrogenic Clover," *Aust. J. agric. Res.*, vol. 18, pp. 647-655, (1967).

Shutt, D.A., "Interaction of Genistein With Oestradiol in the Reproductive Tract of the Ovariectomized Mouse," *J. Endrocrin.*, vol. 37, pp. 231-232, (1967).

Shutt, D.A. et al., "Quantitative Aspects of Phyto-Oestrogen Metabolism in Sheep Fed on Subterranean Clover (*Trifolium subterraneum* Cultivar Clare) or Red Clover (*Trifolium pratense*)," *Aust. J. Agric. Res.*, vol. 21, pp. 713-722, (1970).

Shutt, D.A. et al., "The Significance of Equol in Relation to the Oestrogenic Responses in Sheep Ingesting Clover with a High Formononetin Content," *Aust. J. Agric. Res.*, vol. 19, pp. 545-553, (1968).

Shutt, D.A. et al., "Steroid and Phyto-Oestrogen Binding to Sheep Uterine Receptors In Vitro," J. Endocr., vol. 52, pp. 299-310, (1972).

Siddiqui et al. "Hypolipidemic principles of *Cicer Arietinum*: Biochanin-A and Formononetin," *Lipids*, vol. 11, No. 3, pp. 243-246, (1975).

Smith, A.K. et al. (Eds.), "Solvent Treatment of Beans and Fractions," in *Soybeans: Chemistry and Technology* vol. 1: Proteins, Publishing Co., Inc., Westport, CT, p. 149, (1972).

Smith, A.K. et al. (Eds.), "Phenolic Constituents," in *Soybeans: Chemistry and Technology* vol. 1: Proteins, Avi Publishing Co., Inc., Westport, CT, pp. 187-189, (1972).

Smith, G.R. et al., "Influence of Harvest Date, Cultivar, and Sample Storage Method on Concentration of Isoflavones in Subterranean Clover," *Crop Science*, vol. 26, No. 5, pp. 1013-1016, (Sep.-Oct. 1986).

Stampfer, M. et al., "A Prospective Study of Cholesterol, Apolipoproteins, and the Risk of Myocardial Infarction," *The New England Journal of Medicine*, vol. 325, No. 6, pp. 373-381, (1991).

Statutory Declaration of Fiona Bathgate, declared Mar. 24, 1998, 4 pages.

Amended Statutory Declaration of Fiona Bathgate, declared Oct. 26, 1998, 2 pages.

Statutory Declaration of Nancy Beckham, declared Sep. 8, 1998, 20 pages.

Statutory Declaration of Kerry Martin Bone, declared Oct. 5, 1998, 31 pages.

Statutory Declaration of Jennifer Carpinelli, declared Oct. 21, 1998, 2 pages.

Statutory Declaration of G. Clements, declared Jan. 27, 1999, 2 pages.

Statutory Declaration of Julie Hill, declared Apr. 4, 1998, 2 pages.

Statutory Declaration of Norbert Krause, declared Nov. 5, 1998, 23 pages.

Statutory Declaration of Ngaire Petit-Young, declared Nov. 5, 1998, 3 pages.

Statutory Declaration of Hubert Regtop, declared Nov. 24, 1998, 53 pages.

Statutory Declaration of Joseph Nicolas Van Haaster, declared Jan. 26, 1999, including Exhibit "JNVH-1," 20 pages.

Szabo et al., 1973, "The Selective Reduction of Isoflavon," *Tetrahedron Letters*, 19: 1659-1662.

Trease, G.E. et al., "20: Introduction and General Methods," in *Pharmacognosy*, 12th edition, Bailliére Tindall, Alden Press, Oxford, Great Britain, pp. 241-260, (1983).

Troisi, R.J., et al., "Menopause, Postmenopausal Estrogen Preparations and the Risk of Adult-Onset Asthma," *Am J Respir Crit Care Med*, vol. 152, pp. 1183-1188 (1995).

Verdeal, K. et al., "Naturally-Occurring Estrogens in Plant Foodstuffs—A Review," *J. Food Protect.*, vol. 42, No. 7, pp. 577-583 (Jul. 1979).

Wähälä, K. et al., "Hydrogen Transfer Reduction of Isoflavones," *Heterocycles*, 28(1):183-186 (1989).

Walter, E.D., "Genistin (an Isoflavone Glucoside) and its Aglucone, Genistein, from Soybeans," *J. Am. Chem. Soc.*, vol. 63, pp. 3273-3276, (Jul.-Dec. 1941).

Walz, E., "Isoflavon- und Saponin-Glucoside in Soja hispida," *Justus Liebigs Annalen der Chemie.*, vol. 489, pp. 118-155 (1931).

Wang, C., et al., "Phytoestrogen Concentration Determines Effects on DNA Synthesis in Human Breast Cancer Cells," *Nutrition and Cancer*, 28(3), pp. 236-247, (1997).

Wang, G. et al., "A Simplified HPLC Method for Determination of Phytoestrogens in Soybean and Its Processed Products," *J. Agr. Food Chem.*, vol. 38, No. 1, pp. 185-190 (1990).

Weber, C., "Involvement of Tyrosine Phosphorylation in Endothelial Adhesion Molecule Induction," *Immunologic Research*, No. 15, pp. 30-37, (1996).

Weinberg, D.S. et al., "Identification and Quantification of Anticarcinogens in Garlic Extract and Licorice Root Extract Powder," *Journal of High Resolution Chromatography*, vol. 15, Oct. 1992, p. 641-654.

Welshons, W.V. et al., "Stimulation of breast cancer cells in vitro by the environmental estrogen enterolactone and the phytoestrogen equol," *Breast Cancer Research and Treatment*, vol. 10, 169-175, (1987).

Whalley, W.B.; "5:4'-Dihydroxy-8-Methylisoflavone, and a Note on Lotoflavin," *Journal of the Chemical Society*, pp. 1833-1837., (1957).

White, E. et al., "Extracta," in *Pharmacopedia; A Commentary on the British Pharmacopoeia*, 1898, 2nd Edition Simpkin, Marshall, Hamilton, Kent & Co., Ltd., London, England, pp. 166-167, (1909).

Wilcox, G. et al., "Oestrogenic effects of plant foods in postmenopausal women," *British Med. J.*, vol. 301, pp. 905-906, (Oct. 20, 1990).

Winship, K.A., "Unopposed estrogens," *Adv. Drug React. Ac. Pois. Rev.*, vol. 1, pp. 37-66, (1987).

Wong; E., "Detection and Estimation of Oestrogenic Constituents in Red Clover," *J. Sci. Food Agric.*, vol. 13, pp. 304-308, (May 1962).

Wong, E. et al., "The Oestrogenic Activity of Red Clover Isoflavones and some of Their Degradation Products," *J. Endocrin.*, vol. 24, pp. 341-348, (1962).

Yahara, S. et al., "Isoflavan and Related Compounds from *Dalbergia odorifera*. I", Chem. Pharm. Bull., vol. 37, No. 4, pp. 979-987, (1989).

Bezuidenhoudt, B. C. B. et al., "Synthesis of Isoflavanoid Oligomers Using a Pterocarpan as Inceptive Electrophile", J. Chem. Soc. Perkin Trans. I, pp. 2767-2778, (1984).

Bingham, S. A. et al., "Phyto-oestrogens: Where Are We Now?", British Journal of Nutrition, vol. 79, pp. 393-406, (1998).

Brandt, E.V. et al., "Direct synthesis of the first natural bi-isoflavonoid," *Chem. Comm.*24:1409-1410 (1982).

International Search Report for PCT/AU02/00264, dated May 17, 2002, 2 pages.

Supplementary Partial European Search Report for EP 02 70 4471, dated Jul. 4, 2005, 2 pages.

Weidenbörner, M. et al., "Antifungal Activity of Isoflavonoids in Different Reduced Stages on *Rhizoctonia solani* and *Sclerotium rolfsh*," Phytochemistry 29(3):801-803 (1990).
Pending claims for U.S Appl. No. 09/602,191.
Allowed claims for U.S. Appl. No. 09/546,565.
Pending claims for U.S. Appl. No. 09/986,509.
Pending claims for U.S. Appl. No. 10/176,762.
Pending claims for U.S. Appl. No. 10/177,387.
Pending claims for U.S. Appl. No. 10/636,902.
Pending claims for U.S. Appl. No. 11/024,512.
Pending claims for U.S. Appl. No.10/947,356.
Pending claims for U.S. Appl. No. 10/459,537.
Pending claims for U.S. Appl. No. 10/851,270.
Pending claims for U.S. Appl. No. 10/704,385.
Pending claims for U.S. Appl. No. 10/181,549.
Pending claims for U.S. Appl. No. 10/250,858.
Pending claims for U.S. Appl. No. 10/471,668.
Pending claims for U.S. Appl. No. 10/493,390.
Pending claims for U.S. Appl. No. 10/510,837.

DIMERIC ISOFLAVONES

FIELD OF THE INVENTION

The present invention generally relates to novel dimeric molecules based on the 1,2-diphenylpropane (isoflavonoid) ring structure. The present invention further relates to the synthesis of the dimeric isoflavonoid molecules, compositions containing the same and their use as therapeutic agents.

BACKGROUND OF THE INVENTION

Naturally-occurring plant isoflavones are known to possess a wide range of fundamental biological effects on human cells including anti-oxidation and the up-regulation and down-regulation of a wide variety of enzymes and signal transduction mechanisms. Mitotic arrest and cytotoxicity of human cancer cells, increased capillary permeability, increased cellular adhesion, increased response of vascular smooth muscle cells to vaso-relaxants, and agonism of estrogen receptors, are just a few examples of the responses of animal cells to the biological effects of naturally-occurring isoflavonoids.

A range of therapeutic benefits as a result of these biological outcomes have been identified including the treatment and prevention of pre-menopausal symptoms such as pre-menstrual syndrome, endometriosis, uterine fibroids, hyperlipidaemia, cardiovascular disease, menopausal symptoms such as osteoporosis and senile dementia, alcoholism, benign prostatic hypertrophy, and cancers such as prostate, breast and large bowel carcinomas [see WO 93/23069; WO 96/10341; U.S. Pat. No. 5,424,331; JP 62-106017; JP 62-106016; U.S. Pat. No. 5,516,528; JP 62-106016A2; JP 62-106017A2; JP 61-246124; WO 98/50026; WO 99/43335; WO 00/49009; WO 00/644,438; WO 99/48496].

While over 700 different naturally occurring isoflavones are described, only a few are confirmed as having potential therapeutic benefits in animals including humans. These include daidzein, genistein, formononetin, biochanin and glycitein. These and all naturally occurring isoflavones are found in nature as the monomeric form either in a free state, or, more likely, bound to a carbohydrate moiety (glycoside). The isoflavone has to be separated from this moiety before it becomes biologically active.

A number of compounds with a structure related to naturally occurring plant isoflavones are also described as having biological properties with potential therapeutic benefit to animals including humans. These include compounds that are naturally occurring metabolites of plant isoflavones produced by bacterial fermentation by gut flora and embrace compounds such as equol and O-desmethylangolensin [WO 93/23069; WO 98/08503; WO 01/17986; WO 00/66576]. Also included in this group is the synthetic isoflavonoid ipriflavone, which is developed for the treatment of post-menopausal osteoporosis [WO 91/14429] and a wide range of synthetic isoflavonoid analogues [WO 98/08503].

Recently, some interest has been expressed in the biological properties of dimeric forms of isoflavonoids. Four forms of bis-isoflavones with the following structures are claimed to have 5-alpha-reductase inhibitory activity useful for the treatment of prostatomegaly [JP 9067362-A].

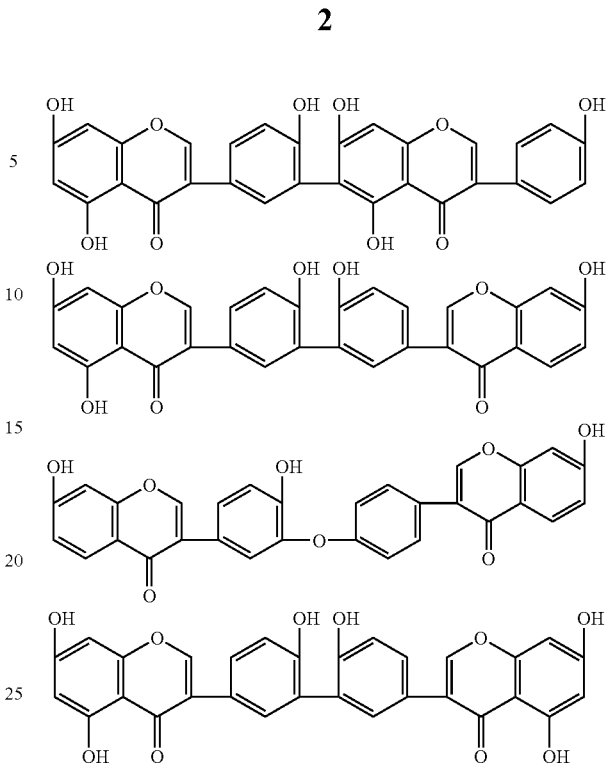

A C—C bridged bis-isoflavone dimer as shown below has also been described, but no biological activity or therapeutic benefit has been ascribed to it [Al-Maharik et al].

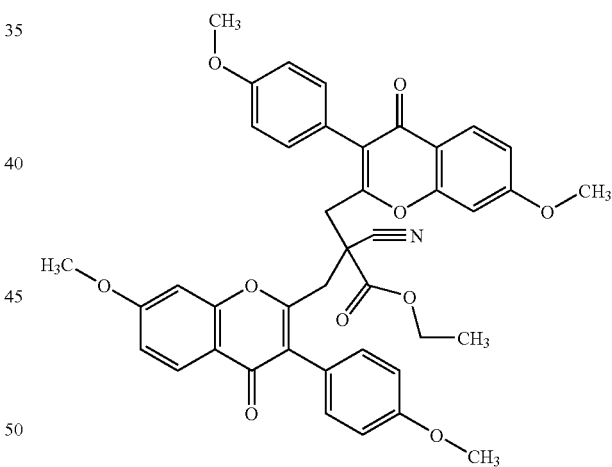

A requirement accordingly exists for new generation compounds that exhibit important pharmacological effects for use as prophylactics and in therapy.

SUMMARY OF THE INVENTION

Surprisingly, the present inventors have discovered a new class of molecules based on dimeric isoflavone compounds and derivatives. The dimeric molecules of the present invention generally show strong binding affinity for both estrogen receptors and hence exhibit remarkable physiological activity.

Thus according to a first aspect of the present invention there is provided a compound of the general formulae (I) or (II):

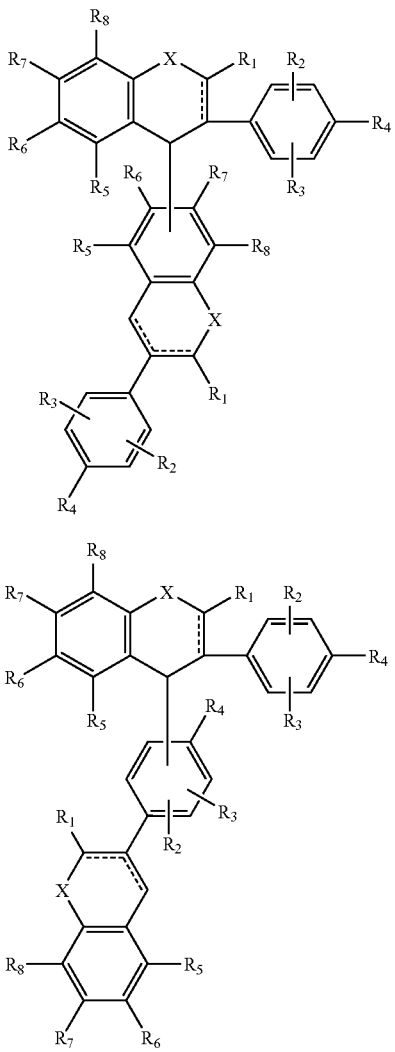

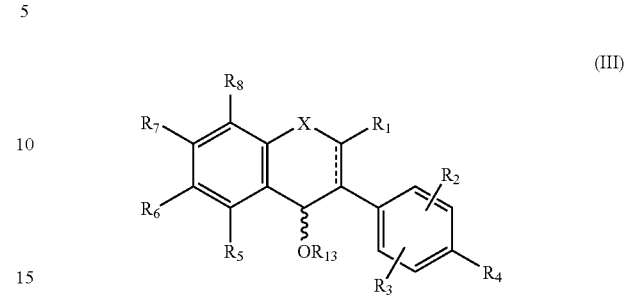

wherein $R_1$, $R_2$, $R_3$, $R_4$, $R_5$, $R_6$, $R_7$ and $R_8$ are independently hydrogen, hydroxy, $OR_9$, OC(O)H, OC(O)$R_9$, OS(O)$R_9$, OSi$(R_{10})_3$, C(O)$R_{11}$, $CO_2R_{12}$, alkyl, haloalkyl, aryl, arylalkyl, thio, alkylthio, amino, alkylamino, dialkylamino, nitro or halo, $R_9$ is alkyl, haloalkyl, aryl, arylalkyl or alkylaryl, $R_{10}$ is independently hydrogen, alkyl or aryl, $R_{11}$ is hydrogen, alkyl, aryl, arylalkyl or an amino acid, and $R_{12}$ is hydrogen, alkyl, haloalkyl, aryl or arylalkyl, x is O, $NR_4$ or S, and the drawing "-----" represents either a single bond or a double bond, which compounds include pharmaceutically acceptable salts thereof, with the proviso that in formula (1) at least one of $R_5$, $R_6$, $R_7$ and $R_8$ is hydrogen.

According to a second aspect of the present invention there is provided a process for the preparation of a compound of formulae (I) or (II) by reacting a compound of the formula (III)

wherein $R_1$, $R_2$, $R_3$, $R_4$, $R_5$, $R_6$, $R_7$ and $R_8$ are independently hydrogen, hydroxy, $OR_9$, OC(O)H, OC(O)$R_9$, OS(O)$R_9$, OSi$(R_{10})_3$, C(O)$R_{11}$, $CO_2R_{12}$, alkyl, haloalkyl, aryl, arylalkyl, thio, alkylthio, amino, alkylamino, dialkylamino, nitro or halo, $R_9$ is alkyl, haloalkyl, aryl, arylalkyl or alkylaryl, $R_{10}$ is independently hydrogen, alkyl or aryl, $R_{11}$ is hydrogen, alkyl, aryl, arylalkyl or an amino acid, and $R_{12}$ is hydrogen, alkyl, haloalkyl, aryl or arylalkyl, $OR_{13}$ is hydroxy, another leaving group or an electron withdrawing group, x is O, $NR_4$ or S, and the drawing "-----" represents either a single bond or a double bond, which compounds include pharmaceutically acceptable salts thereof, with the proviso that in the preparation of compounds of formula (I) at least one of $R_5$, $R_6$, $R_7$ and $R_8$ is hydrogen, with a coupling agent.

It has surprisingly been found by the inventors that isoflavone dimers of the general Formulae (I) and (II) have particular utility and effectiveness in the treatment, prophylaxis, amelioration defence against, and/or prevention of one of more of the following diseases and disorders (for convenience hereinafter referred to as the "therapeutic indications"):

(a) all forms of cancer (pre-malignant, benign and malignant) in all tissues of the body. In this regard, the compounds may be used as the sole form of anti-cancer therapy or in combination with other forms of anti-cancer therapy including but not limited to radiotherapy and chemotherapy;

(b) diseases and disorders associated with inflammatory reactions of an abnormal or prolonged nature in any of the body's tissues including but not limited to rheumatoid artritis, tendonitis, inflammatory bowel disease, ulcerative colitis, Crohn's Disease, sclerosing cholangitis;

(c) papulonodular skin lesions including but not limited to sarcoidosis, angiosarcoma, Kaposi's sarcome, Fabry's Disease (d) papulosquamous skin lesions including but not limited to psoriasis, Bowen's Disease, and Reiter's Disease;

(e) actinic damage characterized by degenerative changes in the skin including but not limited to solar keratosis, photosensitivity diseases, and wrinkling;
(f) diseases and disorders associated with abnormal angiogenesis affecting any tissue within the body including but not limited to hemangiomas and telangiectasia;
(g) proliferative disorders of bone marrow including but not limited to megaloblastic disease, myelodysplastic syndromes, polycythemia vera, thrombocytosis and myelofibrosis;
(h) autoimmune disease characterized by abnormal immunological responses including but not limited to multiple sclerosis, Type 1 diabetes, systemic lupus erythematosis, and biliary cirrhosis;
(i) neurodegenerative diseases and disorders characterized by degenerative changes in the structure of the neurological system including but not limited to Parkinson's Disease, Alzheimer's Disease, muscular dystrophy, Lou-Gehrig Disease, motomeurone disease;
(j) diseases and disorders associated with degenerative changes within the walls of blood vessels including but not limited to atherosclerosis, atheroma, coronary artery disease, stroke, myocardial infarction, hypertensive vascular disease, malignant hypertension, thromboangiitis obliterans, fibromuscular dysplasia;
(k) diseases and disorders associated with abnormal immunological esponses including but limited to dermatomyositis and scleroderma;
(l) diseases and disorders associated with degenerative changes within the eye including but not limited to cataracts, macular degeneration, retinal atrophy.

In particular the isoflavone dimers also surprisingly have been found to have a potent effect on the production and function of reproductive hormones such as estrogens and androgens. As a result of this, these compounds may be used in the treatment and prevention of one or more of the following disorders and diseases:
(a) conditions in women associated with abnormal estrogen/androgen balance including but not limited to cyclical mastalgia, acne, dysmenorrhoea, uterine fibroids, endometriosis, ovarian cysts, premenstrual syndrome, acute menopause symptoms, osteoporosis, senile dementia, infertility; and
(b) conditions in men associated with abnormal estrogen/androgen balance including but not limited to benign prostatic hypertrophy, infertility, gynecomastia, alopecia hereditaria and various other forms of baldness.

Thus, according to a third aspect of the present invention there is provided a method for the treatment, prophylaxis or amelioration of a disease or disorder which method includes the step of administering a therapeutically effective amount of one or more compounds of formulae (I) and (II) to a subject.

According to a fourth aspect of the present invention there is provided the use of one or more compounds of formulae (I) and (II) in the manufacture of a medicament for the treatment of disease.

According to a fifth aspect of the present invention there is provided the use of one or more compounds of formulae (I) and (II) as an anti-estrogen or selective estrogen receptor modulator (SERM).

According to a sixth aspect of the present invention there is provided an agent for the treatment, prophylaxis or amelioration of a disease which agent comprises one or more compounds of formulae (I) or (II).

According to a seventh aspect of the present invention there is provided a pharmaceutical composition which comprises one or more compounds of formulae (I) and. (II) in association with one or more pharmaceutical carriers and/or excipients.

According to a eighth aspect of the present invention there is provided a drink or food-stuff, which contains one or more compounds of formulae (I) and (II).

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

DETAILED DESCRIPTION OF THE INVENTION

The dimeric molecules of the present invention are structurally related to monomeric isoflavone compounds and derivatives thereof. The term "isoflavone" as used herein is to be taken broadly to include ring-fused benzopyran molecules having a pendent phenyl group from the pyran ring based on a 1,2-diphenylpropane system. Thus, the classes of compounds generally referred to as isoflavones, isoflavenes, isoflavans, isoflavanones, isoflavanols and the like are generically referred to herein as isoflavones, isoflavone derivatives or isoflavonoid molecules.

The term "alkyl" is taken to mean both straight chain and branched chain alkyl groups such as methyl, ethyl, propyl, isopropyl, butyl, isobutyl, secbutyl, tertiary butyl, and the like. The alkyl group has 1 to 10 carbon atoms, preferably from 1 to 6 carbon atoms, more preferably methyl, ethyl propyl or isopropyl. The alkyl group may optionally be substituted by one or more of fluorine, chlorine, bromine, iodine, carboxyl, $C_1$-$C_4$-alkoxycarbonyl, $C_1$-$C_4$-alkylaminocarbonyl, di-($C_1$-$C_4$-alkyl)-amino-carbonyl, hydroxyl, $C_1$-$C_4$-alkoxy, formyloxy, $C_1$-$C_4$-alkyl-carbonyloxy, $C_1$-$C_4$-alkylthio, $C_3$-$C_6$-cycloalkyl or phenyl.

The term "aryl" is taken to include phenyl and naphthyl and may be optionally substituted by one or more $C_1$-$C_4$-alkyl, hydroxy, $C_1$-$C_4$-alkoxy, carbonyl, $C_1$-$C_4$-alkoxycarbonyl, $C_1$-$C_4$-alkylcarbonyloxy or halo.

The term "halo" is taken to include fluoro, chloro, bromo and iodo, preferably fluoro and chloro, more preferably fluoro. Reference to for example "haloalkyl" includes monohalogenated, dihalogenated and up to perhalogenated alkyl groups. Preferred haloalkyl groups are trifluoromethyl and pentafluoroethyl.

The compounds of the invention include all salts, such as acid addition salts, anionic salts and zwitterionic salts, and in particular include pharmaceutically acceptable salts.

The term "pharmaceutically acceptable salt" refers to an organic or inorganic moiety that carries a charge and that can be administered in association with a pharmaceutical agent, for example, as a counter-cation or counter-anion in a salt. Pharmaceutically acceptable cations are known to those of skilled in the art, and include but are not limited to sodium, potassium, calcium, zinc and quaternary amine. Pharmaceutically acceptable anions are known to those of skill in the art, and include but are not limited to chloride, acetate, citrate, bicarbonate and carbonate.

Dimeric isoflavone molecules and derivatives have only recently appeared in the literature.

Japanese patent application No. JP 9067362-A (Sankyo Co. Ltd.) describes bis-isoflavones joined either by the pendent phenyl groups or by one pendent phenyl group of one monomer to the aromatic benzopyran ring of the other isoflavone monomer. The bis-isoflavones are though to be useful as 5-alpha reductase inhibitors.

The synthesis of C—C bridged bis-isoflavones has also been described by the nucleophilic substitution of 2-bromomethyl isoflavone derivatives (Al-Maharik et al.). The double alkylation reaction gives rise to bridged bis-isoflavones attached through the 2-methyl groups. No activity has been ascribed to these newly synthesised bis-isoflavones.

In contrast, the dimeric molecules of the present invention are linked through the 4-position of the isoflavone pyran ring to either of the two aromatic rings. That is, the 4-position of the pyran ring is linked to the aromatic benzopyran ring (formula I), or to the pendent phenyl group (formula I).

Preferred dimeric molecules of the present invention are depicted by the general formulae (Ia) and (IIa):

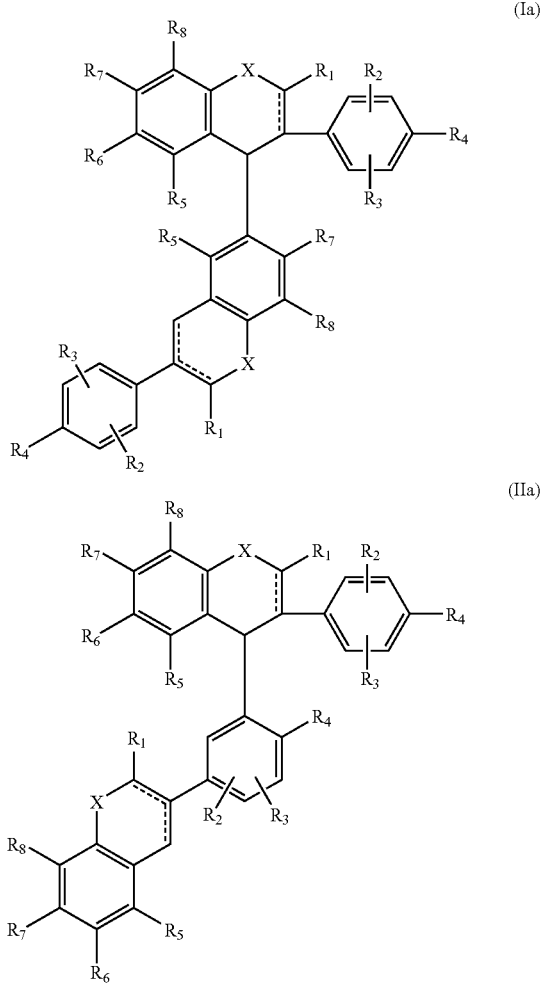

wherein $R_1$, $R_2$, $R_3$, $R_4$, $R_5$, $R_6$, $R_7$ and $R_8$ are independently hydrogen, hydroxy, $OR_9$, $OC(O)H$, $OC(O)R_9$, $OS(O)R_9$, $OSi(R_{10})_3$, $C(O)R_{11}$, $CO_2R_{12}$, alkyl, haloalkyl, aryl, arylalkyl, thio, alkylthio, amino, alkylamino, dialkylamino, nitro or halo, $R_9$ is alkyl, haloalkyl, aryl, arylalyl or alkylaryl, $R_{10}$ is independently hydrogen, alkyl or aryl, $R_{11}$ is hydrogen alkyl, aryl, arylalkyl or an amino acid, and $R_{12}$ is hydrogen, alkyl, haloalkyl, aryl or arylalkyl, X is O, $NR_4$ or S, and the drawing "-----" represents either a single bond or a double bond, which compounds include pharmaceutically acceptable salts thereof, with the proviso that in Formula (Ia) at least one of $R_5$, $R_6$, $R_7$ and $R_8$ is hydrogen;

more preferably they have the following substituents wherein $R_1$, $R_2$, $R_3$, $R_4$, $R_5$, $R_7$ and $R_8$ are independently hydrogen, hydroxy, $OR_9$, $OC(O)R_9$, $OS(O)R_9$, alkyl, aryl, arylalkyl, thio, alkylthio, bromo, chloro or fluoro, $R_6$ is hydrogen, $R_9$ is alkyl, fluoroalkyl or arylalkyl, and X is O;

more preferably they have the following substituents wherein $R_1$ and $R_6$ are hydrogen, $R_2$, $R_3$, $R_5$ and $R_8$ are independently hydrogen, hydroxy, $OR_9$, $OC(O)R_9$, alkyl, aryl or arylalkyl, $R_4$ and $R_7$ are independently hydroxy, $OR_9$ or $OC(O)R_9$, $R_9$ is methyl, ethyl, propyl, isopropyl or trifluoromethyl, and X is O; and most preferably they have the following substituents wherein $R_1$ and $R_6$ are hydrogen, $R_2$, $R_3$, $R_5$ and $R_8$ are independently hydrogen, hydroxy, $OR_9$, $OC(O)R_9$ or methyl, $R_4$ and $R_7$ are independently hydroxy, $OR_9$ or $OC(O)R_9$, $R_9$ is methyl, and X is O.

Most preferably the novel dimeric compounds of formulae (I) and (II) are:

Tetraacetoxy 6-(4-(isoflavan-4',7-diol))-isoflav-3-ene-4',7-diol (2)

6-(4-(Isoflavan-4',7-diol))-isoflav-3-ene-4',7-diol (3)

Tetraacetoxy 6-(4-(isoflavan-4',7-diol))-isoflavan-4',7-diol (4)

6-(4-(Isoflavan-4',7-diol))-isoflavan-4',7-diol (5)

6-(4-(4',7-Dimethoxyisoflavan))-4',7-dimethoxyisoflav-3-ene (6)

6-(4-(4',7-Dimethoxyisoflavan)-4',7-dimethoxyisoflavan (7)

Tetraacetoxy 3'-(4-(isoflavan-4',7-diol))-isoflav-3-ene-4',7-diol (8)

3'-(4-(Isoflavan-4',7-diol))-isoflav-3-ene-4',7-diol (9)

Tetraacetoxy 3'-(4-(isoflavan-4',7-diol))-isoflavan-4',7-diol (10)

3'-(4-(Isoflavan-4',7-diol))-isoflavan-4',7-diol (11)

Compounds 2-11 are depicted by the following structural formulae:

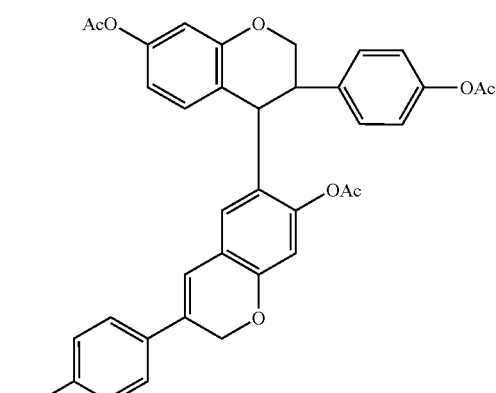
(2)
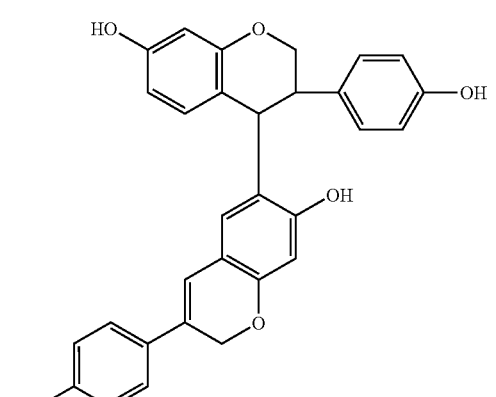
(3)
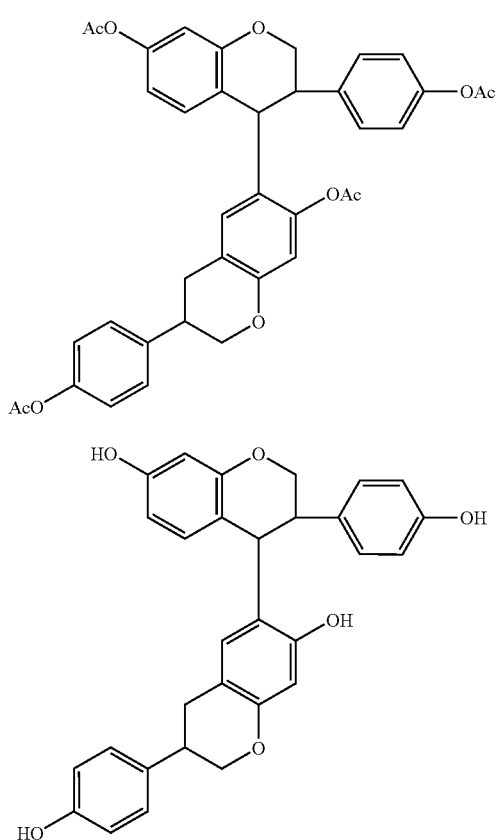
(4)
(5)
-continued
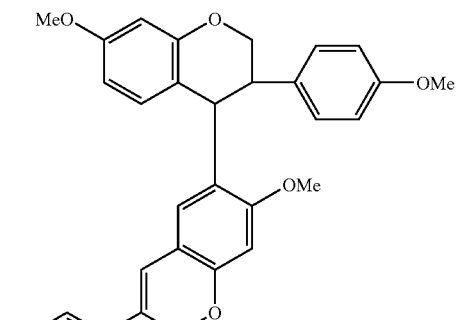
(6)
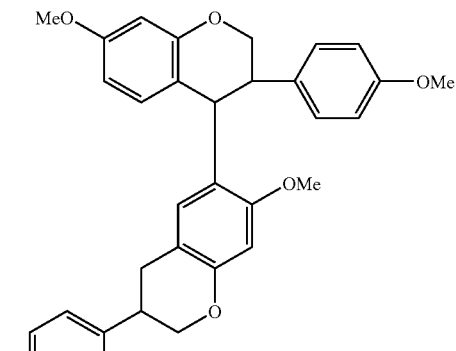
(7)
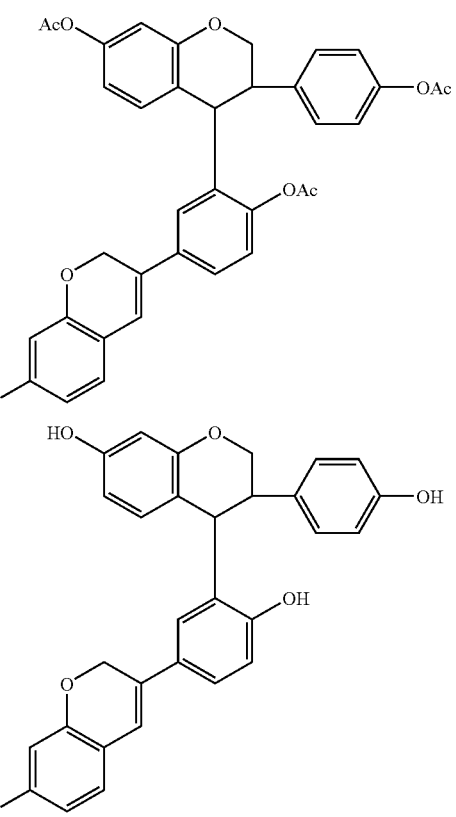
(8)
(9)

-continued

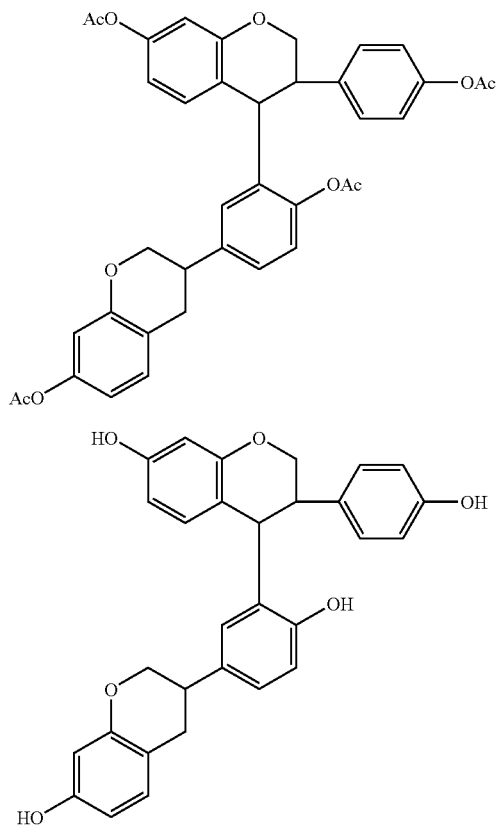

Without wishing to be limited to theory, it is believed that the dimeric molecules of the present invention are formed as a result of an electrophilic aromatic substitution of one of the aromatic rings. Generally, plant-based isoflavone compounds have hydroxy groups in the 4'- and 7-positions, at least, on the isoflavone skeleton. These electron donating groups are thought to assist the electrophilic aromatic substitution and to direct substitution ortho or para to the electron donating substituent.

In a particularly preferred embodiment of the invention, the isoflavone diacetoxy tetrahydrodiadzein (1), R=Ac, is coupled to form a dimeric molecule upon dehydration of the monomer with phosphorus pentoxide.

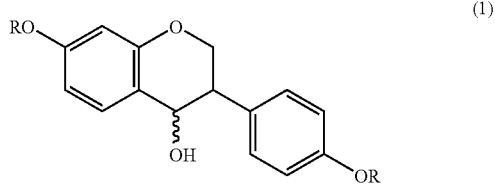

Electrophilic substitution of the ring-fused benzene ring of (1) occurs preferentially alpha to the 7-oxy substituent and beta to the ring junction. The beta position is thought to be more available due to smaller steric constraints than that of the position alpha to the ring junction. The pyran oxygen is thought to assist in the selectivity of substitution by activation of the ring fused benzene to electrophilic aromatic substitution, in preference to substitution of the pendent phenyl group.

Other synthetic methods well known to those skilled in the art may also be employed in the synthesis of the dimeric molecules of the present invention. Such other suitable synthetic methods include Friedel-Crafts alkylation coupling of two isoflavones or derivatives thereof. Typical Friedel-Crafts reaction conditions are used with reagents such as aluminium chloride, boron trifluoride or similar Lewis acid catalysts. The coupling reaction is not limited to Friedel-Crafts type conditions, but may include other reaction conditions that can generate a "carbocation" species such as the conversion of a secondary alcohol to a phosphinic ester or similar facile leaving group. Oxidative coupling reaction conditions such as hydrogen peroxide, dilute permanganate, phosphorous pentoxide or other oxidative compounds may also be employed in the synthesis of the dimeric molecules of the invention.

Linking two monomeric isoflavone compounds or derivatives with a bridging group may also lead to dimeric isoflavone molecules of the present invention Suitable divalent bridging groups include, for example, —O—, —S—, —CH$_2$—, —(C(R)H)$_n$—, —NR—, or —C=O.

Chemical functional group protection, deprotection, synthons and other techniques known to those skilled in the art may be used where appropriate to aid in the synthesis of the compounds of the present invention, and their starting materials.

The preferred starting isoflavone monomer, diacetoxy tetrahydrodaidzein (1) R=Ac, may be obtained by standard procedures known in the art. Particular reference is made to published International patent applications WO 98/08503 and WO 00/49009, and references cited therein, (Novogen Research Pty Ltd) for useful synthetic methods for the production of (1) and related isoflavones.

However, the isoflavone monomers for use in the present invention may be derived from any number of sources readily identifiable to a person skilled in the art. By way of example, the isoflavones may be purchased commercially or extracted from plant sources. Those skilled in the art will readily be able to identify suitable plant species which may be used to derive suitable isoflavone extracts for use in the present invention, however, plants of particular use in the invention include chickpea, soy and clover species, for example. More preferably, an isoflavone extract is obtained from red clover or subterranean clover species.

An isoflavone extract may be prepared by any number of techniques known in the art. For example, suitable isoflavone extracts may be prepared by water/organic solvent extraction from the native plant source. It will be appreciated that an isoflavone extract may be prepared from any single tissue of a single species of plant or a combination of two or more different tissues thereof. Similarly, an extract may be prepared from a starting material which contains a heterogeneous mixture of tissues from two or more different species of plant.

Generally, where an isoflavone extract is prepared from plant material, the material may be comminuted or chopped into smaller pieces, partially comminuted or chopped into smaller pieces and contacted with water and an organic solvent, such as a water miscible organic solvent. Alternatively, the plant material is contacted with water and an organic solvent without any pre-treatment. The ratio of water to organic solvent may be generally in the range of 1:10 to 10:1 and may, for example, comprise equal proportions of water and solvent, or from 1% to 30% (v/v) organic solvent. Any organic solvent or a mixture of such solvents may be used. The organic solvent may preferably be a C2-10, more preferably a C1-4 organic solvent (such as methanol, chloroform, ethanol, propanol, propylene glycol, erythrite, butanol, butanediol, acetonitrile, ethylene glycol, ethyl acetate, glycidol, glycerol dihydroxyacetone or acetone). Optionally the water/organic solvent mixture may include an enzyme which cleaves isoflavone glycosides to the aglycone form. The mixture may be vigorously agitated so as to form an emulsion. The temperature of the mix may range, for example, from an ambient temperature to boiling temperature. Exposure time may be between one hour to several weeks. One convenient extraction period is twenty-four hours at 90° C. The extract may be separated from undissolved plant material and the organic solvent removed, such as by distillation, rotary evaporation, or other standard procedures for solvent removal. The resultant extract containing water soluble and non-water soluble components may be dried to give an isoflavone-containing extract, which may be formulated with one or more pharmaceutically acceptable carriers, excipients and/or auxiliaries according to the invention.

An extract made according to the description provided in the previous paragraphs may contain small amounts of oil which include isoflavones in their aglycone form (referred to herein as isoflavones). This isoflavone enriched oil, may be subject to HPLC to adjust the isoflavone ratios, or, if it is at the desired isoflavone ratio, may be dried, for example in the presence of silica, and be formulated with one or more carriers, excipients and/or auxiliaries to give an isoflavone containing extract. Alternatively, the isoflavones contained in said small amounts of oil may be further concentrated by addition to the oil of a non-water soluble organic solvent such as hexane, heptane, octane acetone or a mixture of one or more of such solvents. One example is 80% hexane, 20% acetone w/w having high solubility for oils but low solubility for isoflavones. The oil readily partitions into the organic solvent, and an enriched isoflavone containing extract falls out of solution. The recovered extract may be dried, for example in an oven at 50° C. to about 120° C., and formulated with one or more pharmaceutically acceptable carriers, excipients and/or auxiliaries.

Other suitable methods may be found in, for example, Chang et al which discloses methods appropriate for the synthesis of various isoflavones and derivatives thereof.

The dimeric isoflavone structures depicted in formulae (Ia) and (IIa) possess an inherent ability to restrict the conformation between the two monomeric structures to an orthogonal relationship. It is hypothesised that the apparent greater conformational rigidity of the orthogonal relationship and the inherent ability to define a displacement of H bond donors in the ligand binding domain monomeric section of the dimer leads to moderation of the normal agonistic actions of the monomer for cellular receptors. In most cases that moderation results in up-regulation of the biological activity, while in some cases it results in down-regulation of that activity. That is, the biological profile of the monomer which to a large extent is predictable based on the known structure-function relationship established from the experience with screening large libraries of such compounds, is unpredictable with the dimeric forms. Functions which are moderated with the conversion from the monomeric to the dimeric forms are as follows: absolute levels of agonism and antagonism of hER-α and HER-β as well as the relative levels of agonism/antagonism of both receptor types; inhibition of 5-α-reductase and 17β-steroidaldehydrogenase; anti-oxidation; mitotic arrest and induction of apoptosis of cancer cells; prostaglandin and inflammatory cytokine release; vasoactivity; high density lipoprotein and low density lipoprotein levels.

Thus the present inventors have surprisingly found that the dimeric molecules of the present invention present a family of new compounds that are indicated for the treatment and prevention of a range of important human diseases and disorders set out above. These diseases and disorders include cancers, inflammatory disorders, autoimmune disorders, cardiovascular disorders, and disorders associated with estrogen receptor activation.

In particular, the dimeric compounds of the present invention through their potent ability to inhibit proliferation of cancer cells and to induce apoptosis show use in the prevention and treatment of cancers, a term which any person skilled in the art would understand embraces aberrant growth of both a benign and malignant nature of any or all tissues in the body across epithelial, mesenchymal and neural types. This includes, but is not restricted to, carcinomas, adenocarcinomas, sarcomas, blastomas, adenomas, lymphomas, leukaemias, gliomas and melanoma.

In particular, the dimeric compounds of the present invention through their potent ability to act as h-ERβ agonists are able to provide oestrogenic support in particular to women of peri-menopausal and menopausal age and to prevent and to treat problems generally recognised as representing acute withdrawal of steroidal estrogen such as vasomotor symptoms (hot flushes and night sweats) and emotional symptoms (anxiety, depression, mood swings), problems generally recognised as representing sub-acute withdrawal of steroidal estrogen such as urinary incontinence and bladder prolapse, and problems generally recognised as representing chronic withdrawal of steroidal estrogen such as osteopaenia and osteoporosis, and senile dementia In particular, the dimeric compounds of the present invention through their potent ability to act as h-ERα antagonists are able to prevent or to treat conditions in pre-menopausal women generally regarded as being associated with excessive stimulation of h-ERα receptors and leading to such conditions as cyclic mastalgia, endometriosis, endometrial hyperplasia, uterine fibroids, polycystic ovarian disease, and pre-menstrual syndrome.

In particular, the dimeric compounds of the present invention through their potent ability to induce vasodilation and to reduce vasospasm show use in the treatment and prevention of disorders generally recognised as being associated with vasopression either causally or indirectly and embracing but not limited to hypertension and migraine headache.

In particular, the dimeric compounds of the present invention through their potent ability to antagonise inflammatory processes and to moderate immunological processes show use in the prevention and treatment of disorders generally recognised as being associated with excessive inflammation or dysfunctional immune function and embracing but not limited to inflammatory conditions of the gastrointestinal tract including inflammatory bowel disease, ulcerative colitis, Crohn's disease, and sclerosing cholangitis, and inflammatory disorders of synovial membranes including rheumatoid arthritis.

In particular, the dimeric compounds of the present invention through their potent ability to act as anti-oxidants show use in the prevention and treatment of conditions generally recognised as being associated with oxidation leading to degenerative changes and including but not limited to conditions such as cataracts, actinic damage, and atherosclerosis.

In particular, the dimeric compounds of the present invention through their potent ability to inhibit androgenesis show use in the prevention and treatment of conditions generally recognised as being associated (either causally or indirectly) with aberrant function of androgens and including but not limited to male pattern baldness (alopecia hereditaria) and prostatic adenoma.

The amount of one or more compounds of formulae I and II which is required in a therapeutic treatment according to the invention will depend upon a number of factors, which include the specific application, the nature of the particular compound used, the condition being treated, the mode of administration and the condition of the patient. Compounds of formulae I or II may be administered in a manner and amount as is conventionally practised. See, for example, Goodman and Gilman, *The Pharmacological Basis of Therapeutics*, 1299 (7th Edition, 1985). The specific dosage utilised will depend upon the condition being treated, the state of the subject, the route of administration and other well known factors as indicated above. In general, a daily dose per patient may be in the range of 0.1 mg to 2 g; typically from 0.5 mg to 1 g; preferably from 20 mg to 200 mg.

The production of pharmaceutical compositions for the treatment of the therapeutic indications herein described are typically prepared by admixture of the compounds of the invention (for convenience hereafter referred to as the "active compounds") with one or more pharmaceutically or veterinarily acceptable carriers and/or excipients as are well known in the art.

The carrier must, of course, be acceptable in the sense of being compatible with any other ingredients in the formulation and must not be deleterious to the subject. The carrier or excipient may be a solid or a liquid, or both, and is preferably formulated with the compound as a unit-dose, for example, a tablet, which may contain from 0.5% to 59% by weight of the active compound, or up to 100% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, optical, buccal (for example, sublingual), parenteral (for example, subcutaneous, intramuscular, intradermal, or intravenous) and transdermal administration, although the most suitable route in any given case will depend on the nature and severity of the condition being treated and on the nature of the particular active compound which is being used.

Formulation suitable for oral administration may be presented in discrete units, such as capsules, sachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture such as to form a unit dosage. For example, a tablet may be prepared by compressing or moulding a powder or granules containing the active compound, optionally with one or more accessory ingredients. Compressed tablets may be prepared by compressing, in a suitable machine, the compound of the free-flowing, such as a powder or granules optionally mixed with a binder, lubricant, inert diluent, and/or surface active/dispersing agent(s). Moulded tablets may be made by moulding, in a suitable machine, the powdered compound moistened with an inert liquid binder.

Formulations suitable for buccal (sublingual) administration include lozenges comprising the active compound in a flavoured base, usually sucrose and acacia or tragacanth; and pastilles comprising the compound in an inert base such as gelatin and glycerin or sucrose and acacia.

Compositions of the present invention suitable for parenteral administration conveniently comprise sterile aqueous preparations of the active compounds, which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the compound with water or a glycine buffer and rendering the resulting solution sterile and isotonic with the blood. Injectable formulations according to the invention generally contain from 0.1% to 60% w/v of active compound and are administered at a rate of 0.1 ml/minute/kg.

Formulations suitable for rectal administration are preferably presented as unit dose suppositories. These may be prepared by admixing the active compound with one or more conventional solid carriers, for example, cocoa butter, and then shaping the resulting mixture.

Formulations or compositions suitable for topical administration to the skin preferably take the form of an ointment, cream, lotion, paste, gel, spray, aerosol, or oil. Carriers that may be used include Vaseline, lanoline, polyethylene glycols, alcohols, and combination of two or more thereof. The active compound is generally present at a concentration of from 0.1% to 0.5% w/w, for example, from 0.5% to 2% w/w. Examples of such compositions include cosmetic skin creams.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 M to 0.2 M concentration with respect to the said active compound.

Formulations suitable for transdermal administration may also be delivered by iontophoresis (see, for example, Panchagnula et al) and typically take the form of an optionally buffered aqueous solution of the active compound. Suitable formulations comprise citrate or Bis/Tris buffer (pH 6) or ethanol/water and contain from 0.1 M to 0.2 M active ingredient.

The active compounds may be provided in the form of food stuffs, such as being added to, admixed into, coated, combined or otherwise added to a food stuff. The term food staff is used in its widest possible sense and includes liquid formulations such as drinks including dairy products and other foods, such as health bars, desserts, etc. Food formulations containing compounds of the invention can be readily prepared according to standard practices.

Formulations suitable for inhalation may be delivered as a spray composition in the form of a solution, suspension or emulsion. The inhalation spray composition may further comprise a pharmaceutically acceptable propellant such as carbon dioxide or nitrous oxide.

The compositions of the invention may also be administered to a human in a dietary supplement form. Dietary supplements incorporating the actives can be prepared by adding the composition to a food in the process of preparing the food. Any food may be used including, but not limited thereto, meats such as ground meats, emulsified meats and marinated meats; beverages such as nutritional beverages, sports beverages, protein fortified beverages, juices, milk, milk alternatives, and weight loss beverages; cheeses such as hard and soft cheeses, cream cheese, and cottage cheese; frozen desserts such as ice cream, ice milk, low fat frozen desserts, and non-dairy frozen desserts; yogurts; soups; puddings; bakery products; salad dressings; and dips and spreads such as mayonnaise, margarine, butter, butter substitute, and other fat containing spreads. The composition is added to the food in an amount selected to deliver a desired dose of the composition to the consumer of the food.

Compounds of the present invention have potent antioxidant activity and thus find wide application in pharmaceutical and veterinary uses, in cosmetics such as skin creams to prevent skin ageing, in sun screens, in foods, health drinks, shampoos, and the like.

It has surprisingly been found that compounds of the formulae I or II interact synergistically with vitamin E to protect lipids, proteins and other biological molecules from oxidation.

Accordingly a further aspect of this invention provides a composition comprising one or more compounds of formulae I and II, vitamin E, and optionally a pharmaceutically, veterinarially or cosmetically acceptable carriers and/or excipients.

Therapeutic methods, uses and compositions may be for administration to humans or animals, such as companion and domestic animals (such as dogs and cats), birds (such as chickens, turkeys, ducks), livestock animals (such as cattle, sheep, pigs and goats) and the like.

As used herein, the term "treatment" is to be considered in its broadest context. The term does not necessarily imply that an animal is treated until total recovery. Accordingly, "treatment" includes amelioration of the symptoms or severity of a particular condition or preventing or otherwise reducing the risk of developing a particular condition.

A "pharmaceutically acceptable carrier, excipient, auxiliary and/or diluent" as used herein should be taken to include any carrier, excipient, auxiliary or diluent that is considered useful in preparing a pharmaceutical composition. Such carriers, excipients, auxiliaries or diluents will be generally safe, non-toxic and neither biologically nor otherwise undesirable. The term also includes carriers, excipients, auxiliaries or diluents that are acceptable for veterinary use as well as human pharmaceutical use. As used herein the term "pharmaceutically acceptable carriers, excipients, auxiliaries and/or diluents" includes one of, or more than one of, such substances.

The invention is further described with reference to the following non-limiting examples.

EXAMPLES

Example 1

Synthesis of Tetra-acetoxy 6(4-(isoflavan-4',7-diol))-isoflav-3-ene-4',7-diol (2)

A mixture of approximately 1:1 cis-and trans-diacetoxytetrahydrodaidzein (1) (300 g) is dissolved in dry dichloromethane and stirred under a bed of nitrogen at 15° C. until all material has dissolved. Phosphorous pentoxide (500 g) is added quickly with vigorous stirring and the reaction is continued for 4-6 hours. The reaction mixture is then filtered through a bed of silica gel with the dimeric structure having a lower $R_f$ than the monomeric side product. The dimeric compound is further purified by selective recrystallisation from ethyl acetate.

$^1$H NMR (CDCl$_3$, 400 MHz): 7.40 (2H, d, J=8 Hz), 7.15 (2H, d, J=8 Hz), 7.13 (2H, d, J=8 Hz), 7.05 (2H, d, J=8 Hz), 6.90 (1H, d J=7.6 Hz), 6.75 (1H, d, J=1.5 Hz), 6.65 (1H, bs s), 6.63 (1H, br s), 6.60 (1H, dd, J=7.6, 1.5 Hz), 6.58 (1H, br s), 5.05 (2H, brs), 4.38 (1H, dd, J=9,3 Hz), 4.30 (1H br d, J=7 Hz), 4.25 (1H, dd, J=9,6 Hz), 3.38 (1H, m), 2.32 (3H, s), 2.30 (3H, s) 2.28 (3H, s), 2.08 (3H, br s)

Example 2

Synthesis of 6(4-(isoflavan-4',7-diol))-isoflav-3-ene-4',7-diol (3)

Imidazole (0.166 g) was added to a suspension of tetraacetoxy 6(4-(isoflavan-4',7-diol))-isoflav-3-ene-4',7-diol (0.2 g) in absolute ethanol (2.0 ml). The mixture was refluxed under nitrogen for 12 hours. The solution was concentrated under vacuum and the product was precipitated by addition of deionised water (10 ml). The mixture was left in the fridge overnight. The off-white solid was filtered and freeze-dried to afford (0.1 g, 67%) of the free phenolic dimeric compound.

$^1$H NMR (D6-DMSO, 400 MHz): 9.1 (4H, br, OH), 7.26 (2H, d, J=7.6 Hz), 7.04 (2H, d, J=7.6 Hz), 6.72 (2H, d, J=7.6 Hz), 6.61 (1H, s), 6.60 (2H, d, J=7.6 Hz), 6.56 (1H, s), 6.46 (1H, d, J=8 Hz), 6.25 (1H, s), 6.22 (1H, brd, J=8 Hz), 6.20 (1H, brs), 4.95 (2H, s), 4.44 (1H, d, J=8.4 Hz), 4.13 (1H, dd, J=11, 3.3 Hz), 4.06 (1H, dd, J=11, 7.7 Hz), 3.28 (1H, ddd, J=8.4, 7.7, 3.3 Hz).

Example 3

Estrogen Receptor Binding Assay

The ability of the tetraphenolic dimer (Structure 3) and tetraacetoxy dimer (Structure 2) to interact with estrogen receptor alpha and beta was determined using a commercially available estrogen receptor binding kit. This kit employs a competitive binding assay to determine the relative binding affinity of test compounds for recombinant human estrogen receptors-alpha (ER-α) and beta (ER-β). Briefly, recombinant human estrogen receptor alpha or beta is added to fluorescently labelled estrogen ligand to form an estrogen ligand/receptor complex which exhibits high fluorescence polarization. The complex is then added to decreasing concentrations of competitor test compounds. The shift in polarization in the presence of test compound is used to determine the relative affinity of test compounds for the estrogen receptor. When assayed using the manufacturer's specifications, we determined the concentration of estradiol required to displace 50% of bound fluorescent estrogen ligand ($EC_{50}$) at 0.011 µM for ER-alpha and 0.006 µM for ER-beta which is in agreement with published values (Bolger et al., 1998). The tetraphenolic dimer (Structure 3) demonstrated equal binding affinity for estrogen receptor alpha and beta (ER-α 0.35±0.05 µM; ER-β 0.37±0.05 µM.), however the tetraacetoxy dimer (Structure 2) did not bind either receptor.

Example 4

Anticancer Activity

The anticancer potential of the tetraphenolic dimer (Structure 3) and the tetraacetoxy dimer (Structure 2) was assessed using a panel of human tumour cell lines, including glioma (C6), prostate (PC3), breast (MCF-7), soft tissue (Kym-1) and lung (NCI-H23 and NCI-H460). The cell cytotoxicity assay was conducted as per the method of Alley et al., 1988. Cell lines are exposed to varying concentrations of test compound for a fixed time. At the conclusion of the assay, the viability of the cell population is determined using the hydrogen acceptor reagent 3-(4,5-dimethylthiazol-2-yl)-2,5 diphenyltetrazolium bromide (MTT). The concentration of compound required to inhibit 50% of cell growth in comparison to a control ($IC_{50}$) is an indicator of effectiveness of the compound. (i.e. the lower the concentration of compound required to inhibit 50% of normal cell proliferation, the more efficacious). Both dimers exhibited potent anticancer activity against the cancer types tested (Table 1).

TABLE 1

IC50 determinations for both dimeric isoflavones against tumour cell lines.

| | Cell Line IC50 (µM) | | | | | |
|---|---|---|---|---|---|---|
| Dimer | MCF-7 | PC3 | C6 Glioma | Kym-1 | NCI-H460 | NCI-H23 |
| Structure 3 | 18 ± 2 | 13.5 | 17.5 | 3.2 | 14.4 | 13.5 |
| Structure 2 | 10 ± 5 | 6 | NT | NT | NT | 7.3 |

NT = not tested

The reference to any prior art in this specification is not, and should not be taken as, an acknowledgment or any form of suggestion that that prior art forms part of the common general knowledge in the field of endeavour.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification individually or collectively, and any and all combinations of any two or more of said steps or features.

REFERENCES

Patents:

JP 9067362-A A; Patent Assignee Sankyo Co Ltd; "New bis-iso-flavone(s) as 5-alpha-reductase inhibitors—prepared from Microbiospora, used for treatment of prostatomegally."

WO 00/49009; Patent assignee Novogen Research Pty Ltd; "Production of Isoflavone derivatives"

WO 91/14429; Chiesi P and Pavesi L Patent; Assignee: Chiesi; "Pharmaceutical compositions containing ipriflavone, process for the preparation thereof and relative therapeutic use."

WO 93/23069; Kelly "GE Health Supplements".

WO 96/10341; Schouten Food and Health Products

U.S. Pat. No. 5,424,331; Shlyankevich; "Pharmaceutical Compositions and Dietary Soybean Food Products for the Prevention of Osteoporosis".

JP 62-106017; Yamanouchi Pharmaceuticals Co Ltd; "Anti-cancer agent for all isoflavonoid agents".

JP 62-106016; Yamanouchi Pharmaceuticals Co Ltd; "Therapeutic claims over isoflavonoids as immuno-suppressive".

U.S. Pat. No. 5,516,528; Hughes et al; "Dietary phytoestrogen in estrogen replacement therapy". (Assignees: Wake Forest Uni and PTJ)

JP 62-106016A2; Immunosuppressor; Yamanouchi Pharmaceutical Co Ltd; "Isoflavones for remedy and the prevention of relapse of autoimmune diseases such as rheumatoid arthritis, SLE etc".

WO 01/17986; Novogen Research; Compositions and therapeutic methods involving isoflavones."

JP 62-106017A2; Anti-tumor agent; Yamanouchi Pharmaceut. Co Ltd; "oncogene originated tyrosine-specific phosphorylase-inhibiting activity".

JP 61-246124; A Carcinostatic Agent; Yamanouchi Pharmaceut. Co Ltd; "carcinostatic agent containing genistein".

WO 98/50026; Kelly G E; "Treatment or prevention of menopausal symptoms or osteoporosis—comprises administering the iso-flavone(s) formononetin or daidzein".

WO 99/43335; Huang L J and Thum M J; "Plant extracts from clover"

WO 00/49009; Heaton A and Kumar N; "Production of isoflavone derivatives".

WO 00/644,438; Husband A J and Kelly G E; "Composition for treatment of cardiovascular diseases and osteoporosis comprises high proportion of formononetin with biochanin, genistein and/or genistein".

WO 99/48496; Husband A J and Kelly G E; "Treating disorders associated with high steroidal estrogen activity e.g. uterine fibroids".

Articles:

Alley M C, Scudiero D A, Monks A, Hursey M L, Czerwinski M J, Fine D L, Abbott B J, Mayo J G, Shoemaker R H, and Boyd M R. 1988. Feasibility of drug screening with panels of human tumor cell lines using a microculture tetrazolium assay. Cancer Res. 48, 589-601

Al-Maharik N I, Kaltia S A A, Mutikainen I, Wahala K Synthesis of C—C-Bridged Bis-Isoflavones *Journal of Organic Chemistry* 65, 2305-2308, 2000

Bingham S A, Atkinson C, Liggins J, Bluck L, Coward A. Phyto-oestrogens: where are we now? *British Journal Of Nutrition* 79(5): 393-406 1998

Bolger R, Wiese T E, Ervin K, Nestich S, Checovich W (1998) Rapid screening of environmental chemicals for estrogen receptor binding capacity. *Environ Health Perspect*; 106, 551-7

Chang Y-C, Nair M G, Santell R C, and Helferich W G. Microwave-mediated synthesis of anticarcinogenic isoflavones from soybeans. *J Agric Food Chem*. 1994, 42, 1869-1871

Goodman and Gilman, *The Pharmacological Basis of Therapeutics*, 1299 7th Edition, 1985

Moss R W, Cancer Therapy: the Independent Consumer's Guide to Non-Toxic Treatment and Prevention (New York: Equinox Press, 1992)

Panchagnula et al. (2000) Transdermal iontophoresis revisited. *Current Opinion in Chemical Biology* 4: 468-473

Scudiero D A, Shoemaker R H, Paull K D, Monks A, Tierney S, Nofziger T H, Currens M J, Seniff D, Boyd M R.

(1988) Evaluation of a soluble tetrazolium/formazan assay for cell growth and drug sensitivity in culture using human and other cell line. *Cancer Res.* 48(17); 4827-33.

The invention claimed is:

1. A compound selected from general formula (Ia):

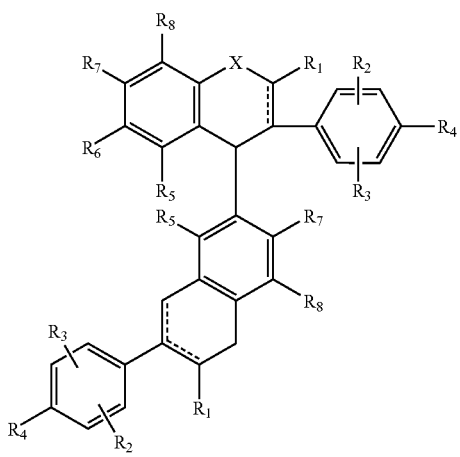

wherein
$R_1$, $R_4$, $R_5$, $R_7$ and $R_8$ are independently hydrogen, hydroxy, $OR_9$, $OC(O)R_9$, $OS(O)R_9$, alkyl, aryl, arylalkyl, bromo, chloro or fluoro,
$R_2$, $R_3$, and $R_6$ are hydrogen,
$R_9$ is alkyl, fluoroalkyl or arylalkyl, and
X is O,
and
the drawing "-----" represents either a single bond or a double bond,
which compounds include pharmaceutically acceptable salts thereof.

2. The compound of claim 1, wherein
$R_1$ is hydrogen,
$R_5$ and $R_8$ are independently hydrogen, hydroxy, $OR_9$, $OC(O)R_9$, alkyl, aryl or arylalkyl,
$R_4$ and $R_7$ are independently hydroxy, $OR_9$ or $OC(O)R_9$, and
$R_9$ is methyl, ethyl, propyl, isopropyl or trifluoromethyl.

3. The compound of claim 2, wherein
$R_5$ and $R_8$ are independently hydrogen, hydroxy, $OR_9$, $OC(O)R_9$ or methyl, and
$R_9$ is methyl.

4. A compound of claim 3 selected from:
Tetraacetoxy 6-(4-(isoflavan-4',7-diol))-isoflav-3-ene-4',7-diol (2),
6-(4-(Isoflavan-4',7-diol))-isoflav-3-ene-4',7-diol (3),
Tetraacetoxy 6-(4-(isoflavan-4',7-diol))-isoflavan-4',7-diol (4),
6-(4-(Isoflavan-4',7-diol))-isoflavan-4',7-diol (5),
6-(4-(4',7-Dimethoxyisoflavan))-4',7-dimethoxyisoflav-3-ene (6), and
6-(4-(4',7-Dimethoxyisoflavan))-4',7-dimethoxyisoflavan (7).

5. A process for the preparation of a compound of formula (Ia)

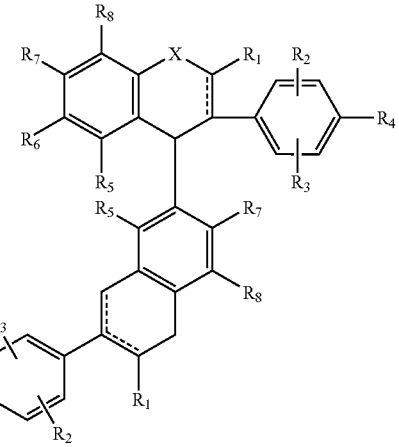

which process comprises reacting a compound of the formula (III)

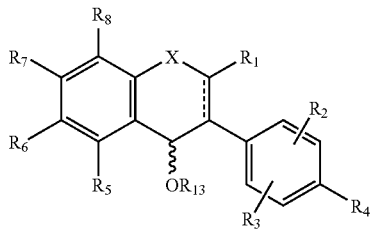

wherein
$R_1$, $R_4$, $R_5$, $R_7$ and $R_8$ are independently hydrogen, hydroxy, $OR_9$, $OC(O)R_9$, $OS(O)R_9$, alkyl, aryl, arylalkyl, bromo, chloro, or fluoro,
$R_2$, $R_3$, and $R_6$ are hydrogen,
$R_9$ is alkyl, fluoroalkyl, or arylalkyl, and
X is O, and
the drawing "-----" represents either a single bond or a double bond,
with a coupling agent to prepare the compound of formula (Ia).

6. The process of claim 5, wherein the compound of formula (Ia) is as defined in any one of claims 3 to 6.

7. The process of claim 5, wherein the coupling agent is phosphorus pentoxide, hydrogen peroxide, permanganate or a Lewis acid.

8. A composition which comprises one or more compounds of formula (Ia) as defined in claim 1 in association with one or more pharmaceutical carriers and/or excipients.

9. A composition comprising one or more compounds of formula (Ia) as defined in claim 1, vitamin E, and optionally a pharmaceutically, veterinarially or cosmetically acceptable carriers and/or excipients.

* * * * *